(12) United States Patent
Janssen-Heininger et al.

(10) Patent No.: US 10,688,150 B2
(45) Date of Patent: *Jun. 23, 2020

(54) TREATMENTS OF OXIDATIVE STRESS CONDITIONS

(71) Applicant: The University of Vermont and State Agricultural College, Burlington, VT (US)

(72) Inventors: Yvonne M. Janssen-Heininger, Charlotte, VT (US); Vikas Anathy, Essex Junction, VT (US)

(73) Assignee: The Univserity of Vermont and State Agricultural College, Burlington, VT (US)

( * ) Notice: Subject to any disclaimer, the term of this patent is extended or adjusted under 35 U.S.C. 154(b) by 70 days.

This patent is subject to a terminal disclaimer.

(21) Appl. No.: 15/874,136

(22) Filed: Jan. 18, 2018

(65) Prior Publication Data

US 2018/0221436 A1    Aug. 9, 2018

Related U.S. Application Data

(63) Continuation of application No. 14/407,265, filed as application No. PCT/US2013/046675 on Jun. 20, 3013, now Pat. No. 9,907,828.

(Continued)

(51) Int. Cl.
*A61K 38/12* (2006.01)
*A61K 38/06* (2006.01)
(Continued)

(52) U.S. Cl.
CPC ............ *A61K 38/12* (2013.01); *A61K 31/197* (2013.01); *A61K 31/425* (2013.01);
(Continued)

(58) Field of Classification Search
None
See application file for complete search history.

(56) References Cited

U.S. PATENT DOCUMENTS 8,877,447 B2   11/2014   Janssen-Heininger et al.
9,907,828 B2 *  3/2018   Janssen-Heininger ..................... A61K 38/06

(Continued)

FOREIGN PATENT DOCUMENTS

WO    WO 2007/083101 A2    7/2007

OTHER PUBLICATIONS

Lawson et al., Proc. Am. Thorac. Soc. 3: 345-349 (2006).*

(Continued)

*Primary Examiner* — Erin M. Bowers
(74) *Attorney, Agent, or Firm* — Wolf, Grreenfield & Sacks, P.C.

(57) ABSTRACT

The present invention generally relates to systems and methods for treating certain oxidative stress conditions. In one aspect, compositions and methods of the invention can be used to treat a subject having an oxidative stress condition, for example, a subject having pulmonary fibrosis. In some embodiments, an inhibitor of ERp57 (for example, thiomuscimol) and/or an inhibitor of GSTP (for example, TLK-199) may be used to treat the subject. Also provided in certain aspects of the present invention are kits for such therapies, methods for promoting such therapies, and the like.

8 Claims, 15 Drawing Sheets

Specification includes a Sequence Listing.

Related U.S. Application Data

(60) Provisional application No. 61/663,458, filed on Jun. 22, 2012.

(51) Int. Cl.

| | | |
|---|---|---|
| *A61K 38/16* | (2006.01) | |
| *A61K 38/45* | (2006.01) | |
| *A61K 45/06* | (2006.01) | |
| *A61K 31/425* | (2006.01) | |
| *A61K 31/437* | (2006.01) | |
| *C12N 15/113* | (2010.01) | |
| *A61K 31/197* | (2006.01) | |
| *A61K 31/713* | (2006.01) | |

(52) U.S. Cl.
CPC .......... *A61K 31/437* (2013.01); *A61K 31/713* (2013.01); *A61K 38/06* (2013.01); *A61K 38/164* (2013.01); *A61K 38/45* (2013.01); *A61K 45/06* (2013.01); *C12N 15/113* (2013.01); *C12N 15/1137* (2013.01); *C12N 2310/14* (2013.01); *C12Y 205/01018* (2013.01); *C12Y 503/04001* (2013.01)

(56) References Cited

U.S. PATENT DOCUMENTS

| | | |
|---|---|---|
| 2009/0202509 A1 | 8/2009 | Leverve |
| 2009/0233888 A1 | 9/2009 | Lin |
| 2010/0266566 A1 | 10/2010 | Janssen-Heininger et al. |
| 2015/0056633 A1 | 2/2015 | Janssen-Heininger et al. |
| 2015/0157686 A1 | 6/2015 | Janssen-Heininger et al. |

OTHER PUBLICATIONS

International Preliminary Report on Patentability dated Dec. 31, 2014 for Application No. PCT/US2013/046675.
International Search Report and Written Opinion dated Sep. 24, 2013 for Application No. PCT/US2013/046675.
[No Author Listed], Wikipedia: Melanoma. <http://web.archive.org/web/20110303161619/http://en.wikipedia.org/wiki/Melanoma>. Archived Mar. 3, 2011. Accessed Sep. 27, 2016. 17 pages.
Anathy et al., Oxidative processing of latent Fas in the endoplasmic reticulum controls the strength of apoptosis. Mol Cell Biol. Sep. 2012;32(17):3464-78. doi: 10.1128/MCB.00125-12. Epub Jul. 2, 2012.
Depeille et al., Combined effects of GSTP1 and MRP1 in melanoma drug resistance. Br J Cancer. Jul. 25, 2005;93(2):216-23.
Gaucci et al., The binding of antibiotics to ERp57/GRP58. J Antibiot (Tokyo). Jun. 2008;61(6):400-2. doi: 10.1038/ja.2008.56.
Hoffstrom et al., Inhibitors of protein disulfide isomerase suppress apoptosis induced by misfolded proteins. Nat Chem Biol. Dec. 2010;6(12):900-6. doi: 10.1038/nchembio.467. Epub Oct. 31, 2010.
Hyoudou et al., PEGylated catalase prevents metastatic tumor growth aggravated by tumor removal. Free Radic Biol Med. Nov. 1, 2006;41(9):1449-58. Epub Aug. 11, 2006.
Ishii et al., Depletion of glutathione S-transferase P1 induces apoptosis in human lung fibroblasts. Exp Lung Res. Oct.-Nov. 2003;29(7):523-36.
Kinnula et al., Oxidative stress in pulmonary fibrosis: a possible role for redox modulatory therapy. Am J Respir Crit Care Med. Aug. 15, 2005;172(4):417-22. Epub May 13, 2005.
Lawson et al., The genetic approach in pulmonary fibrosis: can it provide clues to this complex disease? Proc Am Thorac Soc. Jun. 2006;3(4):345-9.
Lodovici et al., Oxidative stress and air pollution exposure. J Toxicol. 2011;2011:487074. doi: 10.1155/2011/487074. Epub Aug. 13, 2011.
Lovat et al., Increasing melanoma cell death using inhibitors of protein disulfide isomerases to abrogate survival responses to endoplasmic reticulum stress. Cancer Res. Jul. 1, 2008;68(13):5363-9. doi: 10.1158/0008-5472.CAN-08-0035.
O'Brien et al., Glutathione peptidomimetic drug modulator of multidrug resistance-associated protein. J Pharmacol Exp Ther. Dec. 1999;291(3):1348-55.
Raza et al., Phase 1 multicenter dose-escalation study of ezatiostat hydrochloride (TLK199 tablets), a novel glutathione analog prodrug, in patients with myelodysplastic syndrome. Blood. Jun. 25, 2009;113(26):6533-40. doi: 10.1182/blood-2009-01-176032. Epub Apr. 27, 2009.
Song et al., Role of glutaredoxin in metabolic oxidative stress. Glutaredoxin as a sensor of oxidative stress mediated by H2O2. J Biol Chem. Nov. 29, 2002;277(48):46566-75. Epub Sep. 19, 2002.
Sprong et al., Low-dose N-acetylcysteine protects rats against endotoxin-mediated oxidative stress, but high-dose increases mortality. Am J Respir Crit Care Med. Apr. 1998;157(4 Pt 1):1283-93.
Tavender et al., Peroxiredoxin IV protects cells from oxidative stress by removing H2O2 produced during disulphide formation. J Cell Sci. Aug. 1, 2010;123(Pt 15):2672-9. doi: 10.1242/jcs.067843. Epub Jul. 13, 2010.
Uhal, The role of apoptosis in pulmonary fibrosis. Eur Respir Rev. 2008;17(109):136-44.
Wang et al., Structural insights into the peroxidase activity and inactivation of human peroxiredoxin 4. Biochem J. Jan. 1, 2012;441(1):113-8. doi: 10.1042/BJ20110380.

\* cited by examiner

Fig. 1A
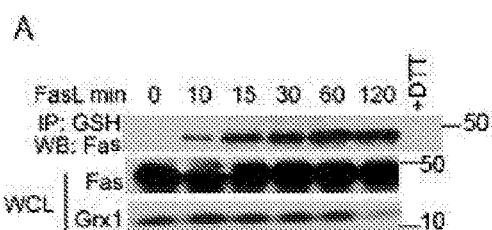
Fig. 1E
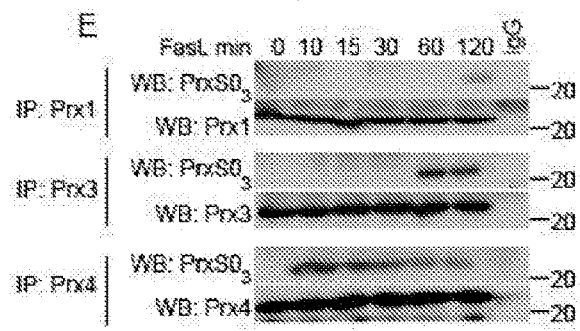
Fig. 1B
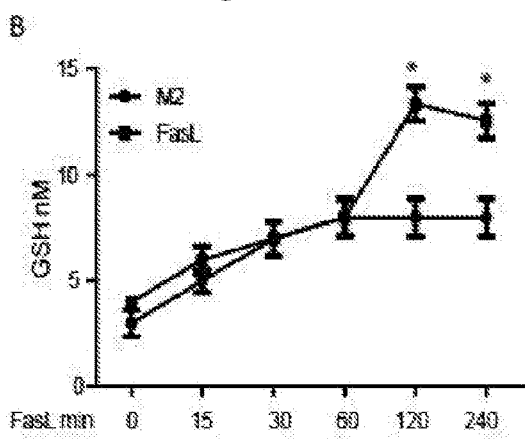
Fig. 1F
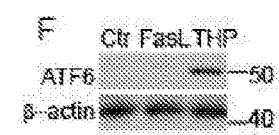
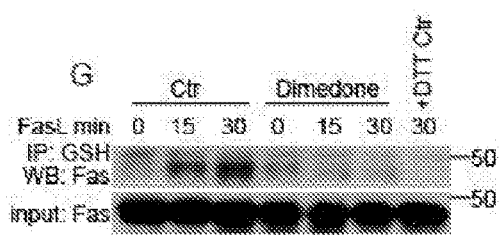
Fig. 1G
Fig. 1C
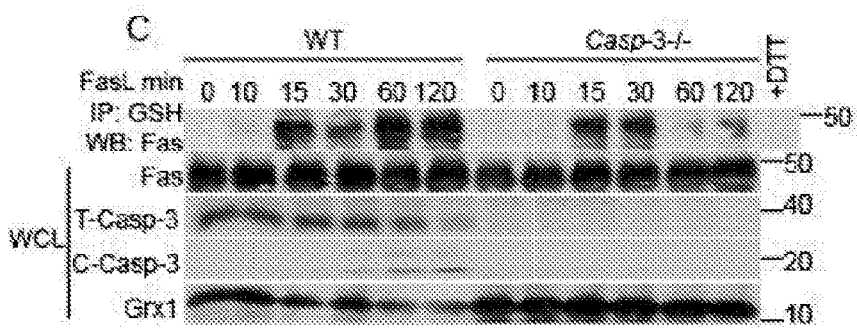
Fig. 1D
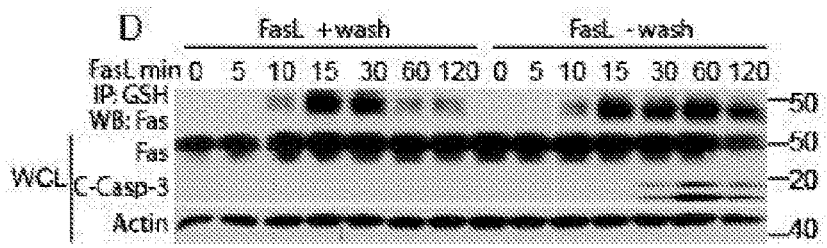

Fig. 2A
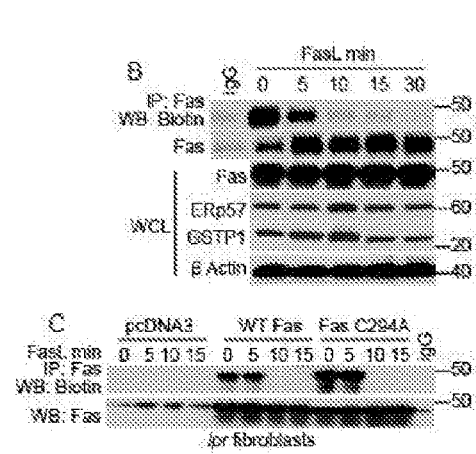
Fig. 2B
Fig. 2C
Fig. 2D
Fig. 2E
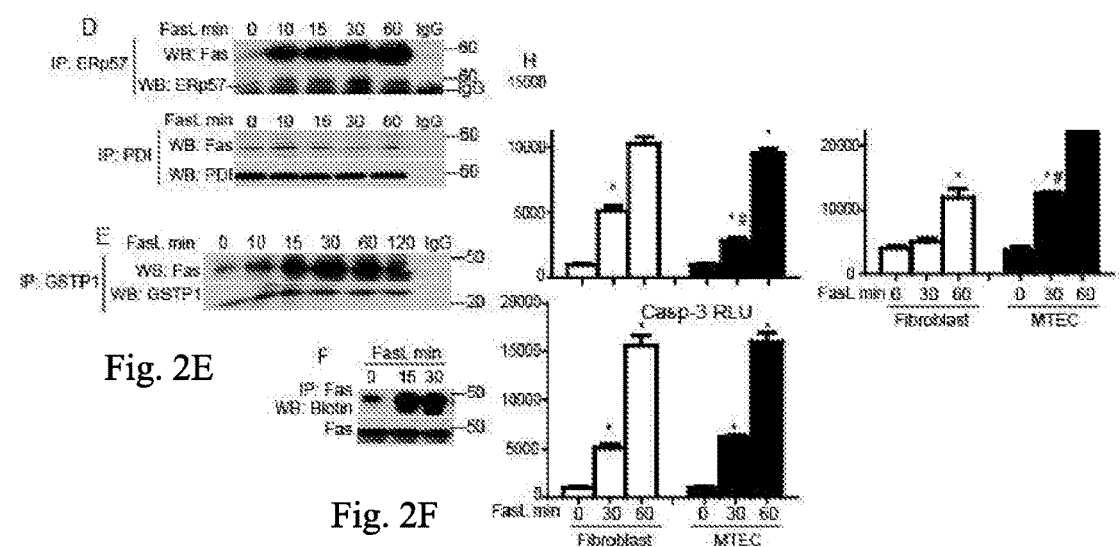
Fig. 2F
Fig. 2G
Fig. 2H
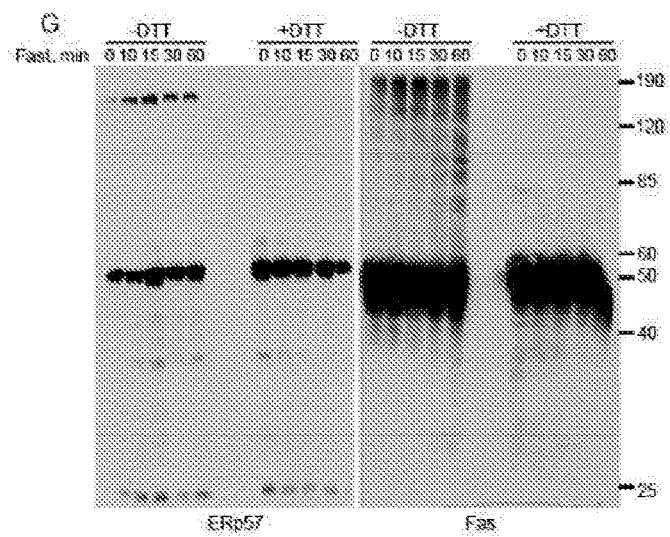

Fig. 2I
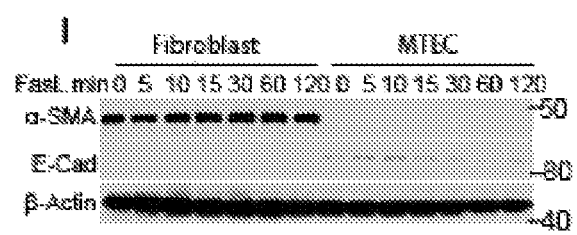
Fig. 2J
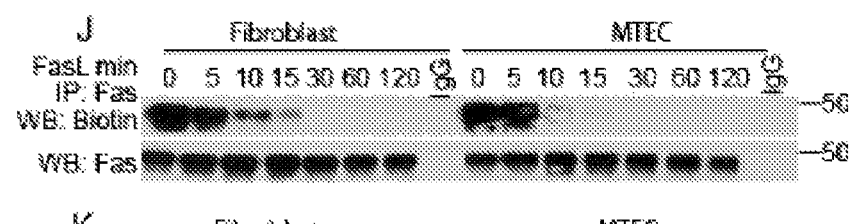
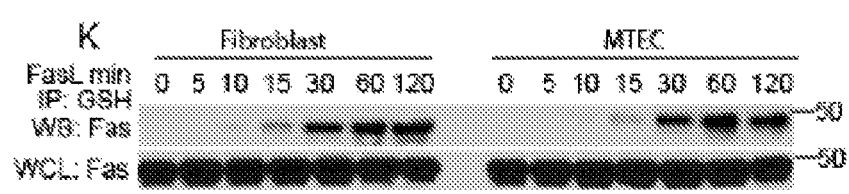
Fig. 2K

Fig. 3A
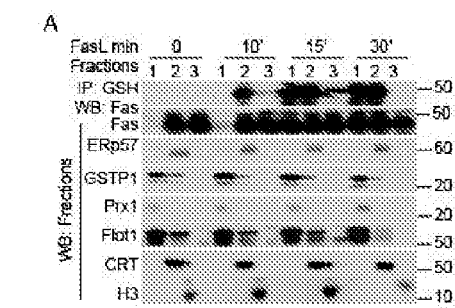
Fig. 3C
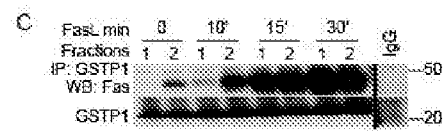
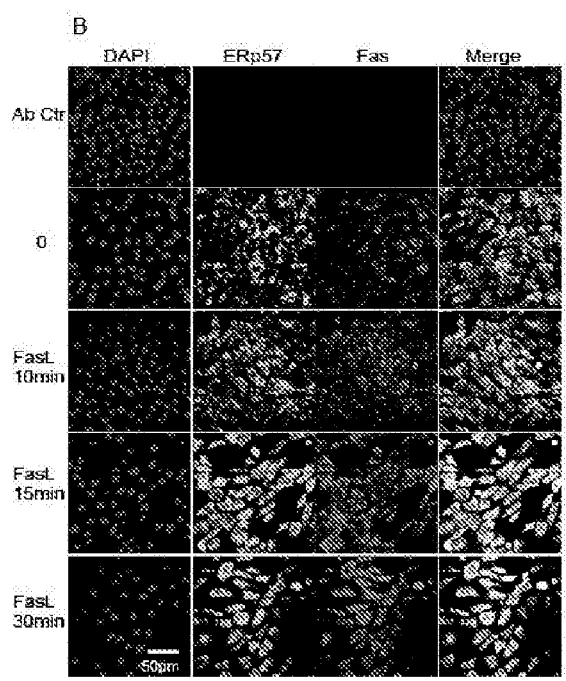
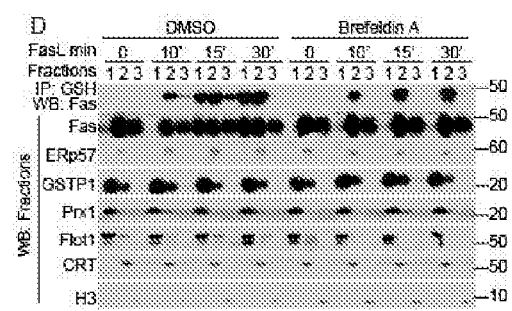
Fig. 3D
Fig. 3B

Fig. 4A
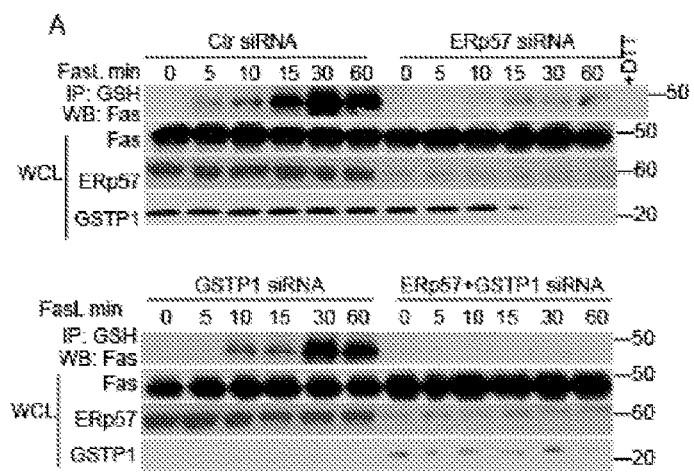
Fig. 4B
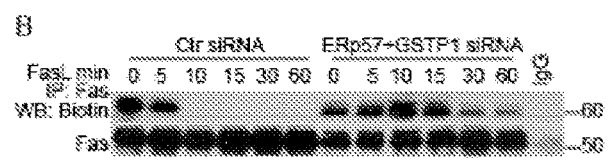
Fig. 4C
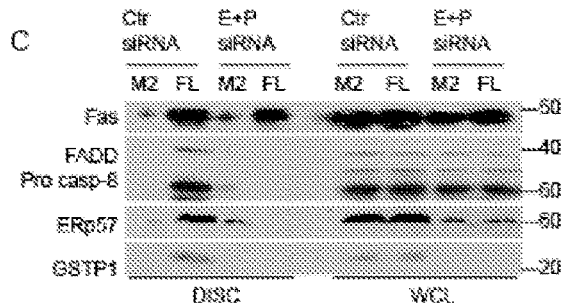
Fig. 4D
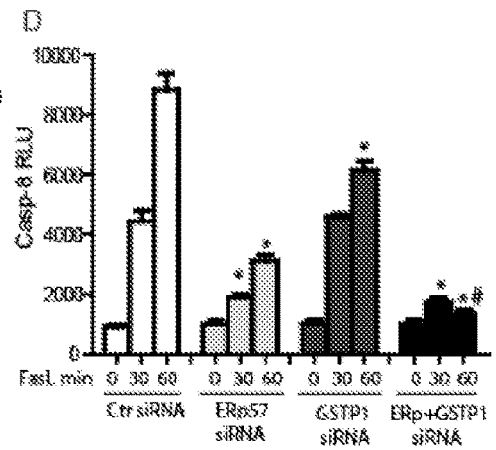
Fig. 4E
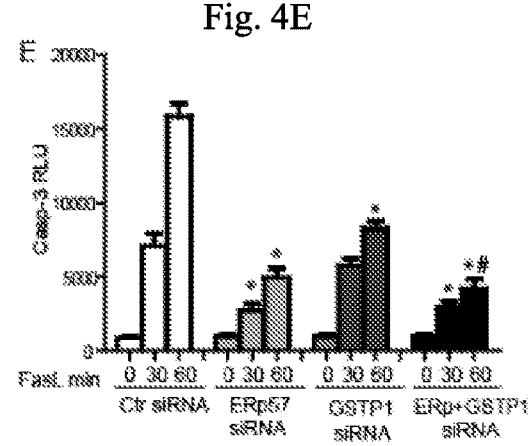
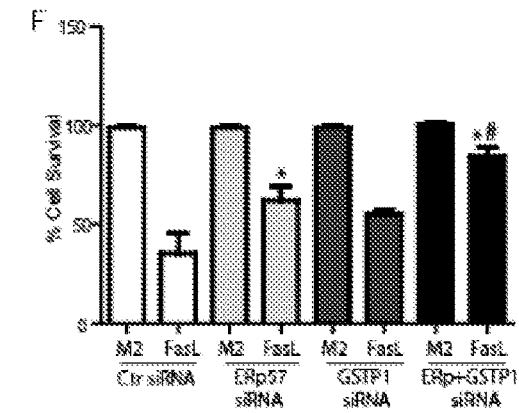
Fig. 4F Fig. 5D
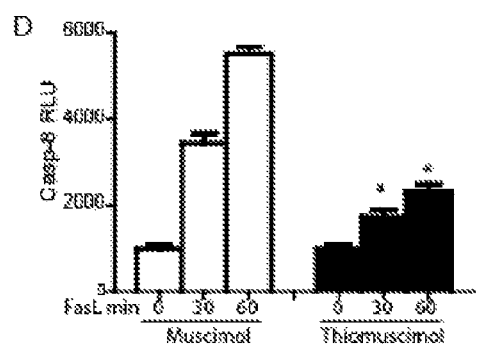
Fig. 5E
Fig. 5I
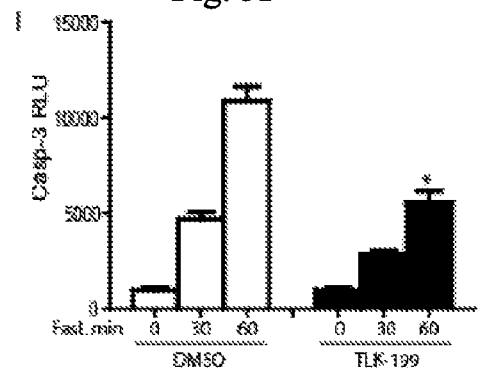
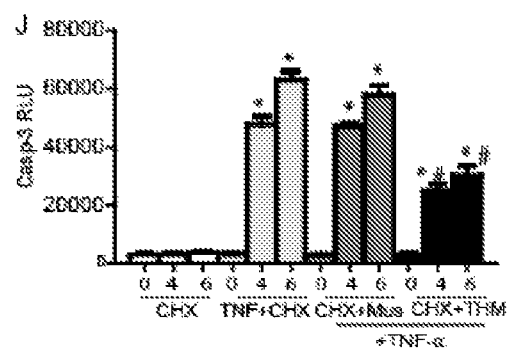
Fig. 5J Fig. 6A
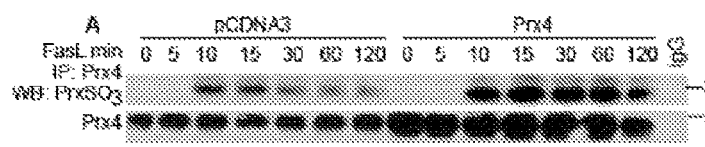
Fig. 6E
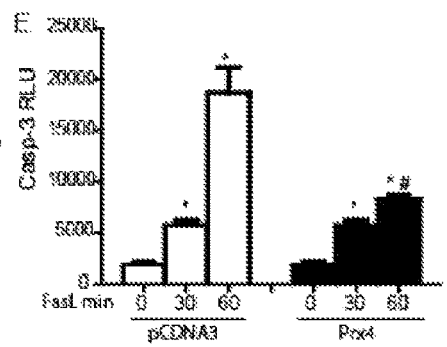
Fig. 6B
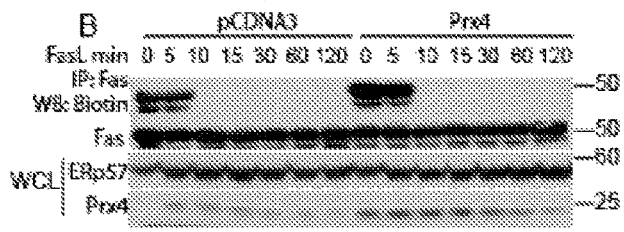
Fig. 6C
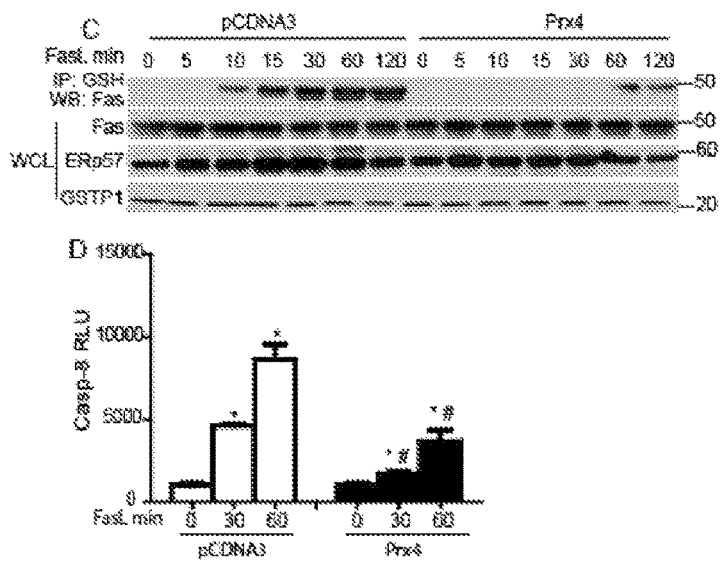
Fig. 6F
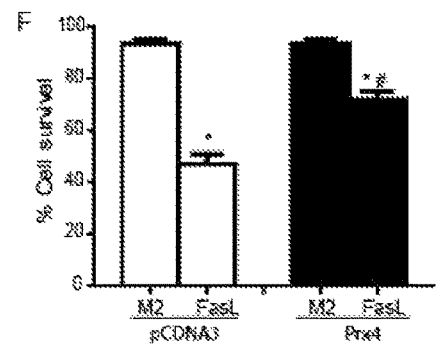
Fig. 6D Fig. 8A
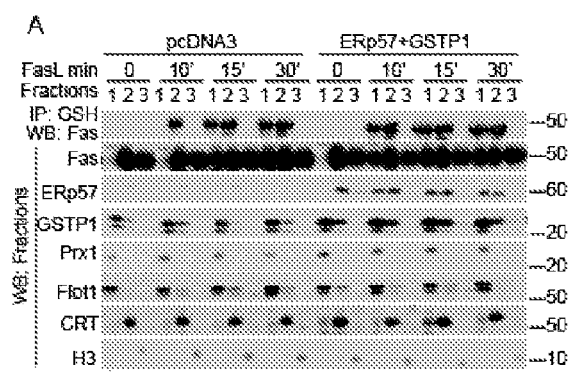
Fig. 8C
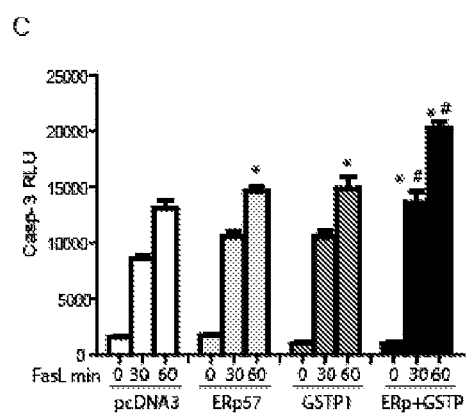
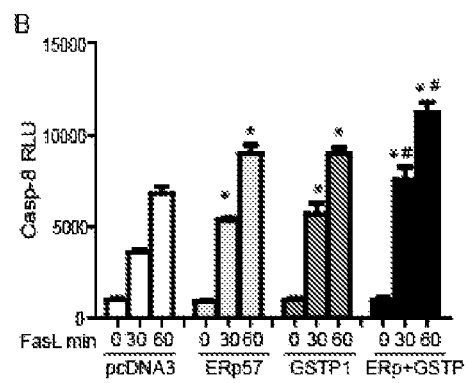
Fig. 8B
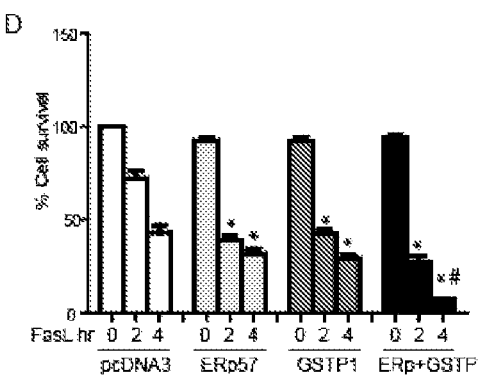
Fig. 8D Fig. 9A
Fig. 9C
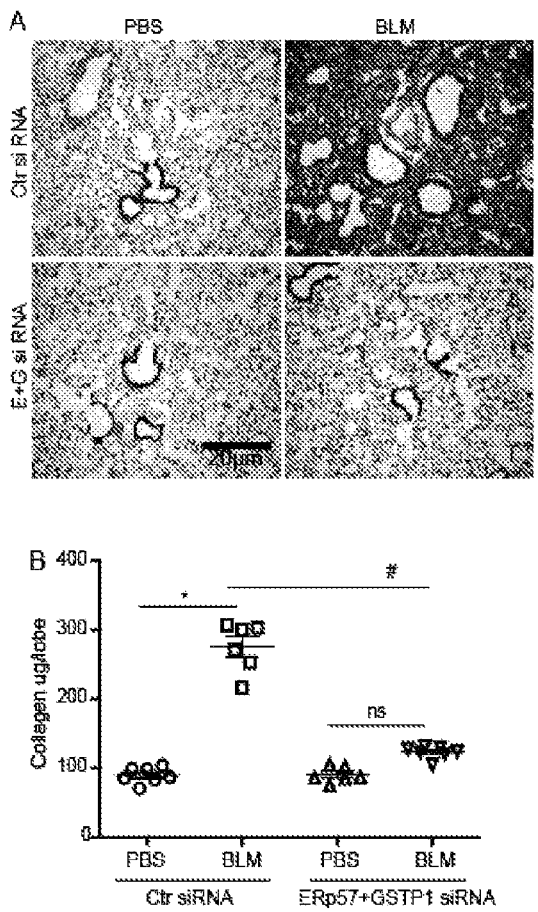
Fig. 9B
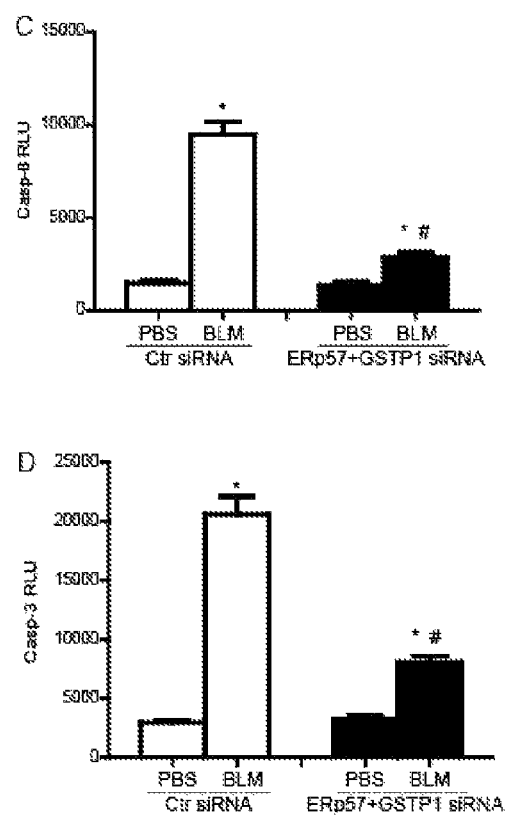
Fig. 9D Fig. 9E
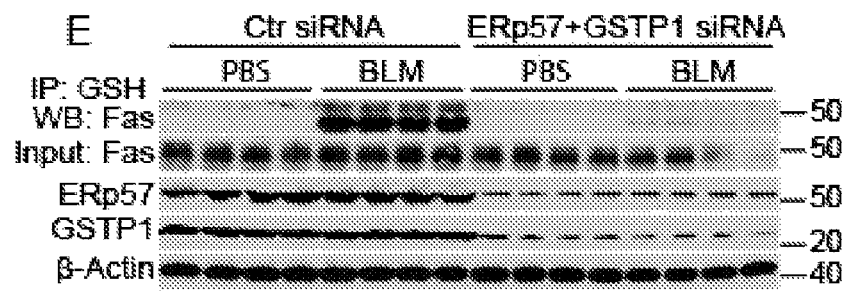
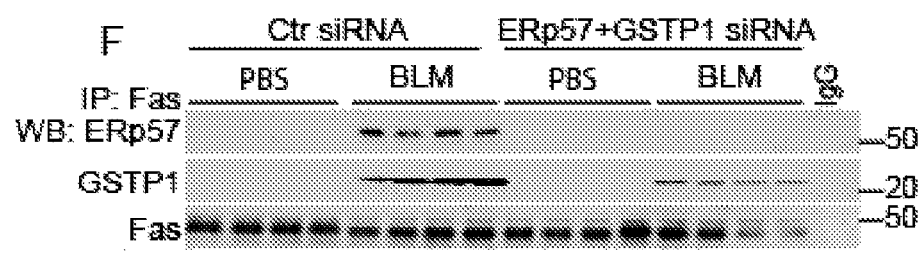
Fig. 9F
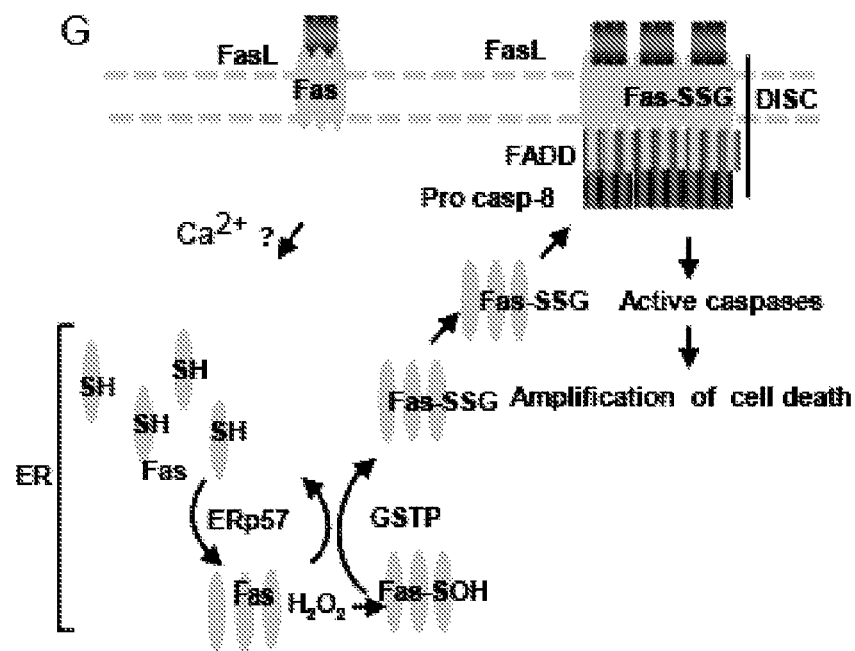
Fig. 9G Fig. 12A
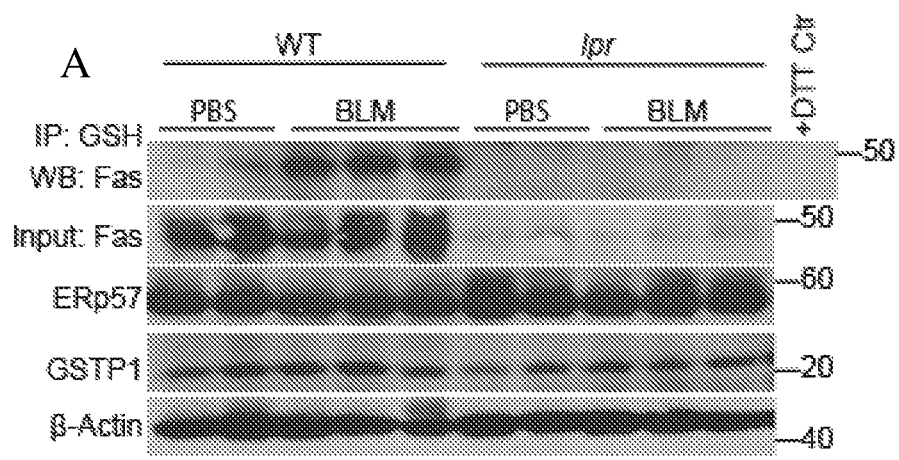
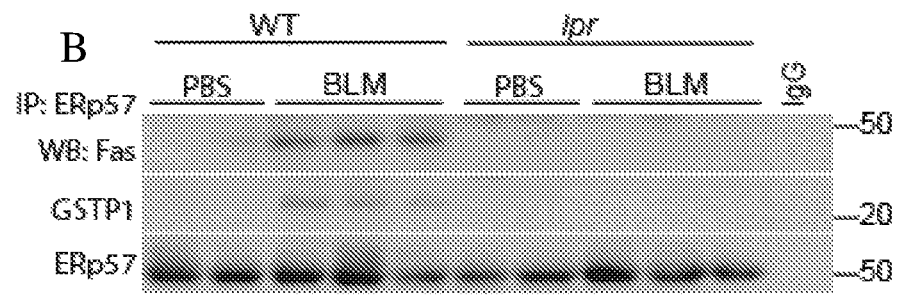
Fig. 12B

TREATMENTS OF OXIDATIVE STRESS CONDITIONS

RELATED APPLICATIONS

This application is a continuation of U.S. patent application Ser. No. 14/407,265, filed Dec. 11, 2014, entitled "Treatments of Oxidative Stress Conditions," by Janssen-Heininger, et al., which is a national stage filing under 35 U.S.C. § 371 of International Application No. PCT/US2013/046675, filed Jun. 20, 2013, which claims the benefit of U.S. Provisional Patent Application Ser. No. 61/663,458, filed Jun. 22, 2012, entitled "Treatments of Oxidative Stress Conditions," by Janssen-Heininger, et al., each of which is incorporated herein by reference.

GOVERNMENT FUNDING

This invention was made with government support under Grant Nos. HL079331, HL060014, HL085464, RR031158, and CA85660 awarded by National Institutes of Health. The government has certain rights in the invention.

FIELD

The present invention generally relates to systems and methods for treating certain oxidative stress conditions.

BACKGROUND

Fas (CD95, Apo-1) is a constitutively expressed member of the tumor necrosis factor (TNF) receptor super family of death receptors that shares a conserved 80 amino acid death domain in their cytoplasmic tail which is critical in apoptosis signaling. Upon ligation of Fas, the sequential association of FADD and pro forms of caspase 8 or 10 leads to the formation of the death inducing signaling complex (DISC) resulting in activation of caspase 8 or 10 and execution of apoptosis.

Fas can be post-translationally modified in a redox-dependent manner via the covalent attachment of the small antioxidant tripeptide, glutathione (GSH). This post-translational modification is known as protein S-glutathionylation. S-glutathionylation of cysteine 294 in the endodomain of murine Fas (Fas-SSG) can be sustained via caspase-dependent degradation of the de-glutathionylating enzyme, glutaredoxin-1 (Grx1). Fas-SSG may be functionally important as it enhances recruitment Fas into lipid rafts, promotes FasL binding, DISC formation, and caspase activation thereby amplifying cell death. However, despite these novel observations, the early events that mediate S-glutathionylation of Fas remain unknown.

SUMMARY

The present invention generally relates to systems and methods for treating certain oxidative stress conditions. The subject matter of the present invention involves, in some cases, interrelated products, alternative solutions to a particular problem, and/or a plurality of different uses of one or more systems and/or articles.

In one aspect, the present invention is generally directed to a method of administering, to a subject having or at risk of pulmonary fibrosis, an inhibitor of ERp57 and/or an inhibitor of GSTP and/or a quencher of $H_2O_2$. In another aspect, the present invention is generally directed to a method of administering, to a subject having or at risk of fibrosis, an inhibitor of ERp57 and/or an inhibitor of GSTP and/or a quencher of $H_2O_2$.

In addition, in yet another aspect, the present invention is generally directed to a method of treating cancer comprising administering to a subject having cancer an effective amount of an inhibitor of ERp57 and/or an inhibitor of GSTP and/or a quencher of $H_2O_2$ to treat the cancer. In still another aspect, the present invention is generally directed to a method of treating a cardiovascular disorder comprising administering to a subject having a cardiovascular disorder an effective amount of an inhibitor of ERp57 and/or an inhibitor of GSTP and/or a quencher of $H_2O_2$ to treat the cardiovascular disorder. In another aspect, the present invention is generally directed to a method of treating a neurodegenerative disorder comprising administering to a subject having a neurodegenerative disorder an effective amount of an inhibitor of ERp57 and/or an inhibitor of GSTP and/or a quencher of $H_2O_2$ to treat the neurodegenerative disorder.

In certain aspects, the present invention is generally directed to a method of treating pulmonary disease comprising administering to a subject having pulmonary disease an effective amount of an inhibitor of ERp57 and/or an inhibitor of GSTP and/or a quencher of $H_2O_2$ to treat the pulmonary disease. In some aspects, the present invention is generally directed to a method of treating cystic fibrosis comprising administering to a subject having cystic fibrosis an effective amount of an inhibitor of ERp57 and/or an inhibitor of GSTP and/or a quencher of $H_2O_2$ to treat cystic fibrosis. The invention, in yet another aspect, is directed to a method of treating asthma comprising administering to a subject having asthma an effective amount of an inhibitor of ERp57 and/or an inhibitor of GSTP and/or a quencher of $H_2O_2$ to treat asthma. In accordance with another aspect, the present invention is generally directed to a method of promoting wound healing comprising administering, to a subject having a wound, an inhibitor of ERp57 and/or an inhibitor of GSTP and/or a quencher of $H_2O_2$. In still another aspect, the present invention is generally directed to a method comprising administering, to a subject having or being at risk for a condition characterized by oxidative stress, a composition comprising an inhibitor of ERp57 and/or an inhibitor of GSTP and/or a quencher of $H_2O_2$.

In addition, in yet another aspect, the present invention is generally directed to a kit comprising a container housing an inhibitor of ERp57 and/or an inhibitor of GSTP and/or a quencher of $H_2O_2$, and instructions for administering components in the kit to a subject having or being at risk for a condition characterized by oxidative stress.

Several methods are disclosed herein of administering a subject with a composition for prevention or treatment of a particular condition. It is to be understood that in each such aspect of the invention, the invention specifically includes, also, the composition for use in the treatment or prevention of that particular condition, as well as use of the composition for the manufacture of a medicament for the treatment or prevention of that particular condition.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1G illustrates Fas S-glutathionylation, in accordance with one embodiment of the invention;

FIGS. 2A-2K illustrates FasL-induced oxidative processing of latent Fas, in another embodiment of the invention (SEQ ID NO:1);

FIGS. 3A-3D illustrate localization of ERp57, Fas, and GSTP in the endoplasmic reticulum, in yet another embodiment of the invention;

FIGS. 4A-4F illustrate knockdown of ERp57 and GSTP, in still other embodiments of the invention;

FIGS. 5A-5J illustrate inhibition of ERp57 and GSTP, in other embodiments of the invention;

FIGS. 6A-6F illustrate the effects of Prx4, in another embodiment of the invention;

FIGS. 8A-8D illustrate overexpression of ERp57 and GSTP, in still another embodiment of the invention;

FIGS. 9A-9G illustrate knockdown of ERp57 and GSTP, in yet other embodiments of the invention;

FIGS. 12A and 12B illustrate that Fas S-glutathionylation is increased in bleomycin-treated mice, in still another set of embodiments.

DETAILED DESCRIPTION

Figure 5A:
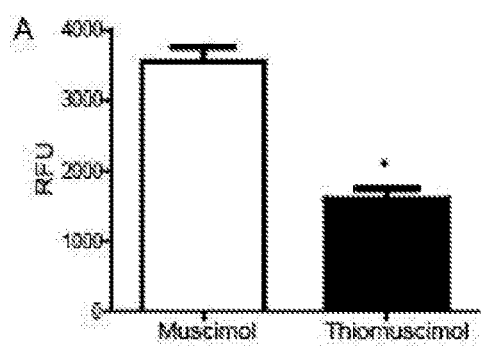

The present invention generally relates to compositions and methods for treating certain oxidative stress conditions. In one aspect, compositions and methods of the invention can be used to treat a subject having an oxidative stress condition, for example, a subject having pulmonary fibrosis. In various embodiments, an inhibitor of ERp57 (for example, thiomuscimol), an inhibitor of GSTP (for example, TLK-199), and/or a composition able to quench $H_2O_2$ in the endoplasmic reticulum may be used to treat the subject. Also provided in certain aspects of the present invention are kits for such therapies, methods for promoting such therapies, and the like.

One aspect of the invention is generally directed to systems and methods for treating certain oxidative stress conditions using inhibitors of ERp57, inhibitors of GSTP, and/or by quenching $H_2O_2$ in the endoplasmic reticulum of cells. Without wishing to be bound by any theory, it is believed that ERp57, GTSP, and $H_2O_2$ are each involved in apoptosis signaling by FasL. In particular, referring now to FIG. 9G, it is believed that ERp57, a protein disulfide isomerase, interacts with Fas, producing hydrogen peroxide ($H_2O_2$) while reducing thiol groups to form disulfide bonds. It is not ERp57 itself that leads to $H_2O_2$, but rather the regeneration of oxidized ERp57, which is believed to be mediated by enzymes such as Ero-1, the latter means that Ero-1 and related enzymes may be a target for intervention. GSTP is an enzyme that interacts with Fas and $H_2O_2$ to cause S-glutathionylation of Fas (i.e., producing Fas-SSG) through a Fas-SOH intermediate. One example of a GSTP is GSTP1. Thus, by disrupting or inhibiting one or both of ERp57 or GTSP, and/or by quenching $H_2O_2$ in the endoplasmic reticulum, apoptosis signaling by FasL may be inhibited or disrupted, which thereby disrupts subsequent processes such as the activation of caspases or the initiation of apoptosis, thereby promoting cell survival and treatment of certain types of oxidative stress conditions.

Thus, various embodiments of the present invention are generally directed to systems and methods for altering the actions of ERp57 and/or GTSP, for instance, by inhibition or by overexpression, and/or by systems and methods for quenching $H_2O_2$ in cells, e.g., in the endoplasmic reticulum. Such interactions may affect the ability of cells to respond to oxidative stress. Accordingly, by altering the actions of ERp57 and/or GTSP, and/or by quenching $H_2O_2$, various oxidative stress conditions may be treated. For example, in some embodiments the oxidative stress condition in a subject may be treated by administering an inhibitor of ERp57 and/or GTSP, and/or a quencher of $H_2O_2$, systemically and/or in the area affected by the oxidative stress. In addition, in some embodiments, the inhibitor of ERp57 and/or GTSP, and/or the quencher of $H_2O_2$ may be delivered to the endoplasmic reticulum in cells. For example, delivery of the inhibitor of ERp57 and/or GTSP, and/or the quencher of $H_2O_2$ to the endoplasmic reticulum may result in beneficial treatment, as discussed herein. In some cases, the inhibitor of ERp57 and/or GTSP, and/or the quencher of $H_2O_2$ may be delivered internally of a cell (e.g., in the cytosol), and allowed to be transported (passively or actively) to the endoplasmic reticulum.

In one set of embodiments, the composition may comprise an inhibitor of ERp57, and/or an inhibitor of a PDI. Examples of suitable inhibitors include, but are not limited to, thiomuscimol or 5-aminomethyl-3-isothiazolol, 16F16, or bacitracin. Thiomuscimol is a structural analog of GABA (gamma-aminobutyric acid) and can inhibit protein disulfide isomerases such as ERp57. Thiomuscimol is available commercially. 16F16 (methyl-2-(2-chloroacetyl)-1-methyl-2,3, 4,9-tetrahydro-1H-pyrido[3,4-b]indole-1-carboxylate) is a PDI inhibitor that is likewise commercially available. Bacitracin generally comprises a mixture of related cyclic polypeptides and is a commercially-available antibiotic.

In some embodiments, the composition may comprise an inhibitor of GSTP. As a non-limiting example, the inhibitor may be TLK-199 or gamma-glutamyl-S-(benzyl)cysteinyl-R-phenyl glycine diethyl ester (ezatiostat or TELINTRA®). TLK-199 is a relatively small molecule that is commercially available.

In certain embodiments, the composition may comprise a quencher of $H_2O_2$. In one set of embodiments, quenching of $H_2O_2$ may be achieved by causing overexpression of Prx4, which is an enzyme that is involved in S-glutathionylation of Fas. Thus, for example, excess Prx4 may be delivered, e.g., to a subject.

In some embodiments, the inhibitor of ERp57 and/or an inhibitor of GSTP and/or a quencher of $H_2O_2$ may be used to target the Fas pathway, e.g., to prevent or inhibit FasL from signaling apoptosis in a cell, thereby decreasing apoptosis or increasing cell survival in a population of cells. In another set of embodiments, the inhibitor of ERp57 and/or an inhibitor of GSTP and/or a quencher of $H_2O_2$ may be used to target other members of the TNF superfamily.

As mentioned, the inhibitor of ERp57 or the inhibitor of GTSP may also comprise an siRNA, in some cases. The siRNAs can be synthesized chemically, or enzymatically. RNase III or DICER can be used to cleave RNA strands to produce siRNAs, or plasmids to may be used to express siRNAs in vivo by delivering them into the target cell using vectors. Techniques for delivering siRNA include electroporation, local or systemic injection, siRNA producing viruses, or transdermal penetration enhancers. Many such siRNAs can be obtained commercially.

For instance, one example of an siRNA that can inhibit ERp57 is ON-TARGETplus SMARTpool, Thermo Scientific Cat No. 14827, having sequences:

```
                                    (SEQ ID NO: 2)
CUUACUAUGAUGUGGACUA (SEQ ID NO: 3)
CCUCAUGACGGAAGAUA (SEQ ID NO: 4)
CAUAUGAAGUCAAGGGUUU (SEQ ID NO: 5)
GUAUGAAGGUGGCCGUGAA
```

In addition, an example of an siRNA that can inhibit GSTP1 is ON-TARGETplus SMARTpool, Thermo Scientific Cat No. 62488, having sequences:

```
                                    (SEQ ID NO: 6)
AGGCAAAGCUUUCAUCGUG (SEQ ID NO: 7)
GGUAAGAAUGACUACGUGA (SEQ ID NO: 8)
CAUACACCAUUGUCUACUU (SEQ ID NO: 9)
CAUACACCAUUGUCUACUU (SEQ ID NO: 10)
AUAGAUACCUGGAUGCAAG
```

In one set of embodiments, a phosphodiester backbone may be incorporated with the siRNA. For example, an siRNA can have at least about 10, 15, 20, 25, or 30 phosphodiester linkages or more incorporated into the backbone. Delivery of the siRNA can be enhanced by the attachment of a modification, such as a cationic group, to at least one end of, or internally on, the sense or antisense strand of the siRNA molecule, or both. Examples of points of attachment include the 5' end of the sense strand, the 3' end of the sense strand or the 3' end of the antisense strand. Exemplary cationic groups include alkyl amines, polyamines, cationic peptides, and cationic amino acids (e.g., arginine, lysine, or ornithine). In one alternative, the cationic group modification can be attached to the 3' end of an siRNA. In another alternative, the cationic group is conjugated internally on the siRNA, e.g., by any of the methods described herein. Lateral conjugation may occur on the sense strand.

An siRNA may also be modified by conjugation of a sugar moiety to the siRNA, in another set of embodiments. Exemplary sugar molecules include glucose, mannose, and 2-deoxy-glucose, and analogs of each. The sugar moiety can include a hydrophobic group, e.g., an alkyl group, attached to the anomeric carbon. For example, the hydrophobic group can be attached via a carbon, sulfur, oxygen, or nitrogen atom, e.g., an amino group. The sugar moiety can be attached to the siRNA, e.g., by a carbamate linker, or by any of the methods described herein.

In another set of embodiments, an siRNA can be conjugated with a substrate for an enzyme or to a protein, e.g., via a lysine residue of the protein. For example, a linker moiety (see infra) can tether the siRNA to the lysine residue. An siRNA-protein conjugate will, in some cases, be more resistant to nucleases than an siRNA alone. After delivery of the siRNA-protein, proteases of the lysosome can optionally liberate the siRNA from the protein conjugate, thereby freeing the siRNA to anneal to a target nucleic acid. In one embodiment, a fusogenic component of the complex, e.g., a fusogenic agent conjugated to the iRNA-protein complex, can facilitate the release of the siRNA from a lysosome or endosome.

An siRNA can also be targeted using a method that relies upon extensive hydration which can be effected, e.g., by conjugation to a moiety, e.g., a polymer, e.g., a polyethylene glycol (PEG). For example, an siRNA can be fused to a water soluble polymer, e.g., a small-molecular weight PEG molecule. The PEG molecule can have a molecular weight of about 500, 600, 900, 1,000, 2,000, 10,000, 25,000, 50,000 or 100,000. For example, the PEG has a molecular weight of between about 500 and about 100,000, or between about 2000 and about 50,000, or between about 5,000 and about 40,000.

An siRNA of the invention can be targeted by conjugation of a peptide containing one or more Arg-Gly-Asp (RGD) motifs. The RGD motif interacts with integrins found on various cells. For example, an iRNA-RGD conjugate can bind to an alphaV-beta3, alpha8, alpha5, or alpha5-beta1 integrin, or to other integrins. In other alternatives, an siRNA of the invention can be conjugated to an RGD analog or RGD mimic.

In some cases, the siRNA may include a region of sufficient homology to a target gene (e.g., ERp57 and/or GTSP), and be of sufficient length in terms of nucleotides, such that the siRNA, or a fragment thereof, can mediate down regulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide," herein can, in the case of a modified RNA or nucleotide surrogate, also refer to a modified nucleotide, or surrogate replacement moiety at one or more positions.) Thus, the siRNA is or includes a region which is at least partially, and in some embodiments fully, complementary to the target RNA. It is not necessary that there be perfect complementarity between the siRNA and the target, but the correspondence must be sufficient to enable the siRNA, or a cleavage product thereof, to direct sequence specific silencing, e.g., by RNAi cleavage of the target RNA, e.g., mRNA.

A single strand siRNA may be sufficiently long that it can enter the RISC and participate in RISC mediated cleavage of a target mRNA. A single strand siRNA may be at least 14, at least 15, 20, 25, 29, 35, 40, or 50 nucleotides in length. It may also be less than 200, 100, or 60 nucleotides in length.

Hairpin siRNA may have a duplex region equal to or at least 17, 18, 19, 29, 21, 22, 23, 24, or 25 nucleotide pairs. The duplex region may be equal to or less than 200, 100, or 50, in length. Examples of ranges for the duplex region are 15-30, 17 to 23, 19 to 23, and 19 to 21 nucleotides pairs in length. The hairpin may have a single strand overhang or terminal unpaired region, e.g., the 3', and/or the antisense side of the hairpin. Some overhangs may be 2-3 nucleotides in length.

It may be desirable to modify one or both of the antisense and sense strands of a double strand RNA. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than 0-Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein, particularly the 5' modifications discussed above in the section on single stranded iRNA molecules.

The sense and antisense strands may be chosen such that the ds siRNA includes a single strand or unpaired region at one or both ends of the molecule. Thus, a ds siRNA contains sense and antisense strands, e.g., paired to contain an overhang, e.g., one or two 5' or 3' overhangs, for instance, a 3' overhang of 2-3 nucleotides. Most embodiments will have a 3' overhang. Some sRNA agents will have single-stranded overhangs, e.g., 3' overhangs, of 1, 2 or 3 nucleotides in length at each end. The overhangs can be the result of one strand being longer than the other, or the result of two strands of the same length being staggered. The 5' ends may be phosphorylated.

Lengths for the duplexed region may be between 15 and 30, or 18, 19, 20, 21, 22, and 23 nucleotides in length, e.g., in the ranges discussed herein. siRNA can resemble in length and structure the natural Dicer processed products from long dsRNAs. Embodiments in which the two strands of the siRNA agent are linked, e.g., covalently linked are also included. Hairpin, or other single strand structures which provide the required double stranded region, and in some cases with a 3' overhang are also contemplated.

In one set of embodiments, the compositions described herein may further comprise one or more glutaredoxins. Glutaredoxins belong to a family of compounds referred to as disulfide reductases. Disulfide reductases are enzymes that reduce disulfide bonds. Examples of disulfide reductases are glutaredoxin (also called thioltransferase), thioredoxin, flavoprotein reductases, the Dsb protein family, ResA and CcdA. Glutaredoxin and thioredoxin are disulfide reductases involved in maintaining cellular thiolredox homeostasis. Glutaredoxins and thioredoxins comprise the family of thiol-didulfide oxidoreductases that are characterized by the thioredoxin fold. Both enzymes catalyze the reversible reduction of protein disulfides. The term glutaredoxin, as used herein, refers to a peptide or nucleic acid encoding a peptide that has at least 80% and more preferably at least 90% homology with a native glutaredoxin peptide or nucleic acid respectively and which maintains at least one biological function of glutaredoxin, even if the potency is less than native glutaredoxin. In some embodiments the potency of the glutaredoxin is at least 50%, 60%, 70%, 80%, 90%, 95% or preferably 98% or greater of native glutaredoxin. A native glutaredoxin is any naturally occurring glutaredoxin.

The glutaredoxins include mammalian glutaredoxins, such a human as well as other organisms. Mammalian glutaredoxins include GRX1, a cytosolic protein with active site Cys-Pro-Tyr-Cys (SEQ ID NO:11), and GRX2 with active site Cys-Ser-Tyr-Cys (SEQ ID NO:12), which may be directed to the mitochondria by a mitochondrial leader sequence and/or can also occur in the nucleus following alternative splicing and GRX5 a mitochondrial glutaredoxin, named GRX5 because it is homologous to yeast GRX5, with only one Cys residue in it active site, Cys-Gly-Phe-Ser (SEQ ID NO:13). Another example of a glutaredoxin is a human lens thioltransferase with 87% homology to human GRX1 and having Cys-Pro-Phe-Cys (SEQ ID NO:14) as active site. Mammalian thioredoxins include the cytosolic TRX1 and the mitochondrial TRX2, both comprising a Gly-Cys-Ser-Cys-Gly (SEQ ID NO:15) active site. TRX1 is involved in the redox regulation of a variety of proteins including transcription factors (for instance NF-κB subunit p50) and proteins involved in the regulation of apoptosis (like ASK-1). Many glutaredoxins are available commercially. For example, GRXs derived from humans or *E. coli* can be obtained from Imco Crop. (Sweden, distributed by American Diagnostica, Stamford, Conn.), or in some cases, glutaredoxins can be prepared recombinantly using methods known to those of ordinary skill in the art or synthetically.

Glutaredoxins have a putative caspase cleavage site which has been shown to be cleaved by caspases in vitro. Modified glutaredoxins include glutaredoxins that have a modified caspase cleavage site. In some embodiments the caspase cleavage site is modified to prevent the site form being cleaved by caspases referred to herein as an inactivated caspase cleavage site. Glutaredoxins with an inactivated caspase cleavage site are particularly embraced by the invention. While all protein modifications are embraced by the invention, it is preferred that the modified glutaredoxin remains biologically active, i.e., can reduce protein disulfides. Compositions and methods comprising a biologically active portion of a glutaredoxin are also embraced by the invention.

A modified glutaredoxin having at least one substitution, deletion or insertion is also useful according to the invention. In some embodiments the glutaredoxin is a glutaredoxin having at least one conservative amino acid substitution from a native glutaredoxin. As used herein, a "conservative amino acid substitution" or "conservative substitution" refers to an amino acid substitution in which the substituted amino acid residue is of similar charge as the replaced residue and is of similar or smaller size than the replaced residue. Typically, the amino acid substitution which does not alter the relative charge or size characteristics of the protein in which the amino acid substitution is made. Such alterations can be prepared according to methods for altering peptide sequence known to one of ordinary skill in the art such as are found in references which compile such methods, e.g. *Molecular Cloning: A Laboratory Manual*, J. Sambrook, et al., Eds., Second Edition, Cold Spring Harbor Laboratory Press, Cold Spring Harbor, N.Y., 1989, or *Current Protocols in Molecular Biology*, F. M. Ausubel, et al., Eds., John Wiley & Sons, Inc., New York.

Conservative substitutions of amino acids include substitutions made amongst amino acids within the following groups (using standard amino acid abbreviations): (a) the small non-polar amino acids, A, M, I, L, and V; (b) the small polar amino acids, G, S, T and C; (c) the amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants. In some embodiments the glutaredoxin has at least 2, 3, 4, 5, 6, 7, 8, 9, 10, 12, 13, 14, 15, 16, 17, 18, 19 or 20 conservative amino acid substitutions.

Methods for making amino acid substitutions, additions or deletions are well known in the art. The terms "conservative substitution," "non-conservative substitutions," "non-polar amino acids," "polar amino acids," and "acidic amino acids" are all used consistently with the prior art terminology. Each of these terms is well-known in the art and has been extensively described in numerous publications, including standard biochemistry text books, such as *Biochemistry* by Geoffrey Zubay, Addison-Wesley Publishing Co., 1986 edition, which describes conservative and non-conservative substitutions and properties of amino acids which lead to their definition as polar, non-polar or acidic. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the glutaredoxin. The activity of functionally equivalent fragments of the glutaredoxin can be tested by cloning the gene encoding the altered enzyme into a bacterial or mammalian expression vector, introducing the vector into an appropriate host cell, expressing the enzyme, and testing for a functional capability of the enzyme as disclosed herein.

Substituting one or more amino acid leads to a modified glutaredoxin that has a certain percentage homology with the native enzyme. Homology is defined as the percentage of amino acids that is the same when a first variant of a glutaredoxin is compared to a second variant of the same enzyme. For instance, if one 1 out of 100 amino acids is different between the two variants than the variants are said to be 99% homologous. Analogously, if 2 out of 100 amino acids are substituted the amino acid is said to be 98% homologous. The invention embraces modified glutoredoxins that are more than 50%, more than 60%, more than 70%, more than 80%, more than 90%, and all values in between, up top 100% homologous to native glutaredoxin.

The modified glutaredoxin having at least one substitution, deletion or insertion may have, in some embodiments, a native conformation. A native conformation as used herein refers to a tertiary structure that is similar to the tertiary structure of native glutaredoxin domain. The tertiary structure of modified or native glutaredoxin domains can be assessed using structural analysis such as crystallography or by functional analysis, such as binding and/or activity assays and NMR spectroscopy. In yet another set of embodiments, the modified glutaredoxin may be a member of the glutathione 5-transferase omega subclass.

Human ERp57 (also known as Protein Disulfide Isomerase A3) has the following primary structure (SEQ ID NO:16):

```
  1  mrlrrlalfp gvalllaaar laaasdvlel tddnfesris dtgsaglmlv effapwcghc
 61  krlapeyeaa atrlkgivpl akvdctantn tcnkygvsgy ptlkifrdge eagaydgprt
121  adgivshlkk qagpasvplr teeefkkfis dkdasivgff ddsfseahse flkaasnlrd
181  nyrfahtnve slvneyddng egiilfrpsh ltnkfedktv ayteqkmtsg kikkfiqeni
241  fgicphmted nkdliqgkdl liayydvdye knakgsnywr nrvmmvakkf ldaghklnfa
301  vasrktfshe lsdfglesta geipvvairt akgekfvmqe efsrdgkale rflqdyfdgn
361  lkrylksepi pesndgpvkv vvaenfdeiv nnenkdvlie fyapwcghck nlepkykelg
421  eklskdpniv iakmdatand vpspyevrgf ptiyfspank klnpkkyegg relsdfisyl
481  qreatnppvi qeekpkkkkk aqedl
```

Human GSTP (Glutathione S-transferase P) has the following primary structure (SEQ ID NO:17):

```
  1  mppytvvyfp vrgrcaalrm lladqgqswk eevvtvetwq egslkascly gqlpkfqdgd
 61  ltlyqsntil rhlgrtlgly gkdqqeaalv dmvndgvedl rckyisliyt nyeagkddyv
121  kalpgqlkpf etllsqnqgg ktfivgdqis fadynlldll lihevlapgc ldafpllsay
181  vgrlsarpkl kaflaspeyv nlpingngkq
```

Human Prx4 (peroxiredoxin 4) has the following structure (SEQ ID NO:18):

```
  1  mealpllaat tpdhgrhrrl lllplllfll pagavqgwet eerprtreee chfyaggqvy
 61  pgeasrvsva dhslhlskak iskpapyweg tavidgefke lkltdyrgky lvfffypldf
```

```
121  tfvcpteiia fgdrleefrs intevvacsv dsqfthlawi ntprrqgglg piripllsdl 181  thqiskdygv yledsghtlr glfiiddkgi lrqitlndlp vgrsvdetlr lvqafqytdk 241  hgevcpagwk pgsetiipdp agklkyfdkl n
```

A variety of subjects and conditions may be treated in various embodiments of the invention. For example, a composition as described above (e.g., comprising one or more of an inhibitor of ERp57, an inhibitor of GSTP, and/or a quencher of $H_2O_2$) may be applied to a subject having or at risk of a disease characterized by oxidative stress. Non-limiting examples of such diseases include fibrosis (e.g., pulmonary fibrosis), asthma, Chronic Obstructive Pulmonary Disease (COPD), Adult Respiratory Distress Syndrome (ARDS), cystic fibrosis, neurodegenerative diseases, various cancers, cardiovascular disorders, wound healing, or others described herein.

Thus, for example, the subject may be one that is at risk of fibrosis, for example, pulmonary fibrosis. Pulmonary fibrosis is generally the formation or development of excess fibrous connective tissue (fibrosis) in the lungs. In some cases, the pulmonary fibrosis may be idiopathic (having no known or apparent cause) and/or familial (genetically linked). In one set of embodiments, the subject carries a mutation in surfactant protein C, which has been linked to pulmonary fibrosis. Without wishing to be bound by any theory, it is believed that such mutations may increase ER (endoplasmic reticulum) stresses in such patients, leading to increased fibrosis (fiber production) in the lungs.

As mentioned, various aspects of the present invention relate to oxidized proteins and glutathionylated proteins. An "oxidized" protein, as used herein, is a protein in which at least one (native) amino acid residue of the protein has been oxidized in some fashion. As an example, glutathione may react with a residue on the protein to glutathionylate the residue. Thus, as used herein, a "glutathionylated" protein is a protein in which at least one amino acid residue of the protein has been glutathionylated, i.e., the amino acid residue has reacted with glutathione, typically through the addition of the glutathione (or a portion thereof) to the residue. Residues that may undergo reactions with glutathione include sulfhydryl moieties (—SH) (e.g., from a cysteine residue), hydroxyl moieties (—OH) (e.g., from a serine residue or a threonine residue), or the like. As a particular example, if the residue includes a sulfhydryl moiety (—SH) (also referred to as a thiol moiety), reaction of the moiety with glutathione can produce an S-glutathionylated moiety, i.e., —S—S-G, where "G" represents glutathione). The "S—" signifies reaction with the sulfhydryl moiety. In some cases, "S-glutathionylation" is also called "S-glutathiolation" or "S-glutathiolation through mixed disulfides."

Thus, the invention relates, in some aspects, to a method of treating a condition characterized by oxidative stress. A condition characterized by oxidative stress is one in which oxidative stress plays a role in the development of the disease or one or more symptoms of the disease. In a subject, an oxidative stress condition may be caused by certain types of chronic diseases or conditions, for example, airway inflammation, Acute Respiratory Distress Syndrome (ARDS), aging, asthmas, emphysema, cancers, rheumatoid arthritis, atherosclerosis, alcohol addition, certain types of cardiovascular disease, certain types of chronic inflammatory diseases, or certain types of neurodegenerative diseases, such as Lou Gehrig's Disease, Parkinson's Disease, Alzheimer's Disease, sporadic amytrophic lateral sclerosis, or Huntington's Disease. Such diseases are often characterized by chronic altered metabolic states in which there are elevated concentrations of certain reactive oxygen species, such as superoxides, singlet oxygens, peroxynitrite, ozone, or hydrogen peroxide. In some embodiments the higher levels or oxidants are caused by inflammation, for instance through the activity of macrophages. In some cases, the reactive oxygen species are created by external factors, such as radiation or ultraviolet light. Other agents that may lead to oxidized proteins include, but are not limited to, chemical reagents such as hydrogen peroxide, $NO_x$ species, or the like, or certain types of biological reactions, such as enzymes that produce oxidative intermediate species (e.g., metabolic enzymes).

The lungs are constantly being exposed to oxygen and are susceptible to oxidative stress. Oxidative stress conditions that can be treated using the present invention include pulmonary diseases such as COPD (chronic obstructive pulmonary disease, also known as chronic obstructive airway disease, which includes chronic bronchitis and/or emphysema), ARDS (acute respiratory distress syndrome), including pulmonary edema, bronchopulmonary dysplasia (BPD), asthma, cystic fibrosis, and pulmonary fibrosis.

Asthma refers to a disorder of the respiratory system characterized by inflammation, narrowing of the airways, and/or increased reactivity of the airways to inhaled agents. Asthma is frequently, although not exclusively, associated with atopic or allergic symptoms. As used herein, a subject having asthma includes those subjects that have been identified as having asthma but that do not have the active disease during the therapy of the invention, as well as subjects that have the active disease of asthma. The airways of asthmatic subjects have elevated levels of Th2 cytokines, especially IL-4 and IL-5. These cytokines promote important aspects of the asthmatic inflammatory response, including IgE isotype switching, eosinophil chemotaxis and activation and mast cell growth. Th1 cytokines, especially IFN-γ (IFN-gamma) and IL-12, can suppress the formation of Th2 clones and production of Th2 cytokines.

Chronic obstructive pulmonary disease (COPD) is used to describe two conditions of fixed airways disease, chronic bronchitis and emphysema. Chronic bronchitis and emphysema are most commonly caused by smoking. COPD is generally characterized by having limited airflow in the lungs and/or a rapid breathing rate, as well as wheezing in the lungs. Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. The airflow obstruction associated with COPD is progressive, may be accompanied by airway hyperreactivity.

Chronic inflammation of the airways is a key pathological feature of COPD. The inflammatory cell population comprises increased numbers of macrophages, neutrophils, and CD8+ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

A broad range of immune and inflammatory cells including neutrophils, macrophages, T lymphocytes and eosinophils contain proteolytic enzymes that could contribute to the destruction of lung extracellular matrix (Shapiro, 1999). In addition, a number of different classes of proteases have been identified that have the potential to contribute to lung matrix destruction. These include serine proteases, matrix metalloproteinases and cysteine proteases. Of these classes of enzymes, a number can hydrolyze elastin and have been shown to be elevated in COPD patients (neutrophil elastase, MMP-2, 9, 12) (Culpitt et al., Am. J. Respir. Crit. Care Med. 160, 1635 39, 1999, Shapiro, Am. J. Crit. Care Med. 160 (5), S29 S32, 1999).

Adult Respiratory Distress Syndrome (ARDS) is a disease of a large number of acute, diffusely infiltrative pulmonary lesions of different etiology if they are associated with a severe gas exchange disorder (in particular arterial hypoxemia). ARDS is generally characterized by inflammation of the lungs which leads to impaired breathing. ARDS can be identified using bilateral infiltrates on chest radiograph, and/or measurements of the partial pressure of oxygen in the lungs and/or the fraction of inspired oxygen.

Triggering causes for ARDS can, for example, be (cited in accordance with Harrison's Principles of Internal Medicine 10th Ed. 1983 McGraw-Hill Int. Book Comp.) diffuse pulmonary infections (for example due to viruses, bacteria, fungi), aspiration of, for example, gastric juice or in the case of near-drowning, inhalation of toxins or irritants (for example chlorine gas, nitrogen oxides, smoke), direct or indirect trauma (for example multiple fractures or pulmonary contusion), systemic reactions to inflammations outside the lung (for example hemorrhagic pancreatitis, gram-negative septicemia), transfusions of high blood volumes or alternatively after cardiopulmonary bypass.

The therapy of ARDS typically comprises different forms of ventilation (for example PEEP (positive end-expiratory pressure), raising of the oxygen concentration of the respiratory air, SIMV (Synchronized Intermittent Mandatory Ventilation; Harrison's Principles of Internal Medicine 10th Ed. 1983 McGraw-Hill Int. Book Comp.)) up to extracorporeal membrane oxygenation (ECMO; Zapol and Lemaire Adult Respiratory Distress Syndrome, Marcel Dekker Inc, 1991).

Bronchopulmonary Dysplasia (BPD) refers to a chronic lung disease that can develop in preterm neonates treated with oxygen and positive-pressure ventilation. BPD results from a variety of factors, including oxidative stress, that can injure small airways and that can interfere with alveolarization (septation), leading to alveolar simplification with a reduction in the overall surface area for gas exchange.

Cystic fibrosis is caused by a mutation in a protein called the cystic fibrosis transmembrane conductance regulator (CFTR). Changes in GSH metabolism have been associated with cystic fibrosis, as the CFTR transporter is regulated by S-glutathionylation. Cystic fibrosis is the most common severe autosomal recessive genetic disorder in the Caucasian population. It affects approximately 1 in 2000 live births in North America (Boat et al, The Metabolic Basis of Inherited Disease, 6th ed, pp 2649-2680, McGraw Hill, NY (1989)). Approximately 1 in 20 persons are carriers of the disease. The major symptoms of cystic fibrosis include chronic pulmonary disease, pancreatic exocrine insufficiency, and elevated sweat electrolyte levels.

Cystic fibrosis (CF) is an autosomal recessive disease characterized by disturbances in ion transport and viscous epithelial mucous secretions. The CF gene protein, CFTR acts as a Cl-channel and is also a key regulator of protein secretion.

Oxidative stress is believed to be a causative or at least ancillary factor in the pathogenesis of major neurodegenerative diseases and aging. In some embodiments the invention is directed to treating a neurodegenerative disease. In some cases the invention contemplates the treatment of subjects having neurodegenerative disease, or an injury to nerve cells which may lead to neuro-degeneration. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc.

"Neurodegenerative disorder" or "neurodegenerative disease" is defined herein as a disorder in which progressive loss of neurons occurs either in the peripheral nervous system or in the central nervous system. Non-limiting examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder or "neurodegenerative disease". In some embodiments the treatment of neurodegenerative disease includes the treatment of Alzheimer's and Parkinson's diseases and in other embodiments the treatment of the disease is excluded.

Most of the chronic neurodegenerative diseases are typified by onset during the middle adult years and lead to rapid degeneration of specific subsets of neurons within the neural system, ultimately resulting in premature death. Compositions such as those described herein may be administered to a subject to treat neurodegenerative disease alone or in combination with the administration of other therapeutic compounds for the treatment or prevention of these disorders or diseases. Many of these drugs are known in the art. For example, antiparkinsonian agents include but are not limited to Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride. Drugs for the treatment of amyotrophic lateral sclerosis include but are not limited to Riluzole. Drugs for the treatment of Paget's disease include but are not limited to Tiludronate Disodium.

Proliferative diseases are characterized by uncontrolled cell growth. Oxidative stress has been associated with proliferative diseases, mostly because of its role in oxidizing proteins and other cellular components, thereby modulating cell signaling and cell growth. In some embodiments the compositions of the present invention can be used to treat proliferative diseases including cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death. Many tumors have altered metabolic demand, including oxidative stresses, and such altered antioxidant defenses may permit tumor growth. Such effects may be countered, at least in part, by the application of the compositions discussed herein. Examples of cancers that can be treated using the compositions of the invention include, but are not limited to biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of the one or more compositions of the invention for treating cancer will be that amount necessary to inhibit mammalian cancer cell proliferation in situ. Those of ordinary skill in the art are well-schooled in the art of evaluating effective amounts of anti-cancer agents.

In some embodiments, the compositions and methods as described herein may be combined with known cancer treatment methods. The term "cancer treatment" as used herein, may include, but is not limited to, chemotherapy, immunotherapy, radiotherapy, adjuvant therapy, surgery, or any combination of these and/or other methods. Particular forms of cancer treatment may vary, for instance, depending on the subject being treated. Examples include, but are not limited to, dosages, timing of administration, duration of treatment, etc. One of ordinary skill in the medical arts can determine an appropriate cancer treatment for a subject.

In some embodiments the cancer medicament is a chemotherapeutic agent selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. In some embodiments the cancer medicament is taxol.

In some embodiments the cancer medicament is an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

The heart is one of the most prominent oxygen-consuming organs and oxidative stress is associated with cardiovascular diseases and heart failures. "Cardiovascular disorders" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies. Other disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, artherosclerosis, and hypertensive vascular disease; inflammatory disease—the vasculitides, such as giant cell (temporal) arteritis, Takayasu arterisis, polyarterisis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

In another aspect, the compositions and methods as described herein are useful in treating wounds in subjects. As used herein, the term "wound" is used to describe skin wounds as well as tissue wounds. A "skin wound" is defined herein as a break in the continuity of skin tissue which is caused by direct injury to the skin. Skin wounds are generally characterized by several classes including punctures, incisions, including those produced by surgical procedures, excisions, lacerations, abrasions, atrophic skin, or necrotic wounds and burns. In some embodiments, the compositions and methods described herein are useful for enhancing or promoting the healing of all wounds of the skin.

A "tissue wound," as used herein, is a wound to an internal organ, such as a blood vessel, intestine, colon, etc. The compositions and methods as described herein may be useful for enhancing the wound healing process in tissue wounds, whether they arise naturally, or as the result of surgery. For instance, during the repair of arteries an artery may need to be sealed and wound healing promoted as quickly as possible. The compositions and methods as described herein may speed up or otherwise enhance that process.

In some embodiments, a composition as described herein may be applied directly to the wound unformulated or in a carrier such as a topical liquid, lotion, or cream, or in any pharmaceutical formulation such as a microcarrier. The compositions may also be attached to a bandage or other substrate, and the substrate positioned over a wound, to completely or at least partially cover the wound. In some cases the bandage or other substrate may be adhered to the subject, for example, through the use of adhesives. Suitable adhesives can be selected by those of ordinary skill in the art.

The compositions of the invention may also be administered with additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors A and B, osteoid-inducing factors, osteogenin and other bone growth factors, collagen growth factors, heparin-binding growth factor 1 or 2, and/or their biologically active derivatives. The compositions may also include antiseptics in some embodiments.

In one embodiment, the oxidative stress condition may be diagnosed within a subject by providing a sample taken from the subject (e.g., a blood sample, cells, fluid, etc.), exposing the sample to a reducing agent, such as an enzyme, able to interact with certain proteins within the sample (e.g., an enzyme or other reducing agent able to react with glutathione or nitroso groups on the protein), and determining if the proteins have been oxidized and in some cases, to what degree.

Other methods of diagnosing an oxidative stress condition are known in the art and include, determining the presence of reactive oxygen species in a subject or sample taken from a subject, wherein reactive oxygen species include singlet oxygen, nitric oxide, superoxide, hydroxy peroxide and peroxynitrite. Oxidative stress may also be diagnosed by determining the presence of oxidized elements in a subject or sample taken from a subject, wherein oxidized elements include oxidized proteins, lipids and nucleic acids. Based on the results of this assay, the subject may be diagnosed as having an oxidative stress condition, which may be indicative of certain diseases, as previously described. The diagnosis of oxidative stress in a subject may be a factor in the decision to initiate the treatment methods of the current invention. Examples of suitable methods of diagnosing an oxidative stress condition are disclosed in U.S. Provisional Patent Application Ser. No. 60/761,956, filed Jan. 25, 2006, entitled "Detection of Glutathionylated Proteins," by Y. Janssen-Heininger; U.S. Provisional Patent Application Ser. No. 60/774,060, filed Feb. 16, 2006, entitled "Detection of Glutathionylated Proteins," by Y. Janssen-Heininger; and U.S. patent application Ser. No. 11/698,300 filed on Jan. 25, 2007, entitled "Detection of Glutathionylated Proteins," by Y. Janssen-Heininger, each of which is incorporated herein by reference.

Any composition of the present invention may be administered to a subject, either by itself and/or in conjunction with co-factors, other therapeutics, or the like. For example, the composition may include an inhibitor of ERp57, an inhibitor of GSTP, and/or a quencher of $H_2O_2$. When administered, the compositions of the invention can be applied in a therapeutically effective, pharmaceutically acceptable amount as a pharmaceutically acceptable formulation, for example, a pharmaceutically acceptable carrier such as those described below. The term "effective amount" of a composition, such as the enzymes of the invention, refers to the amount necessary or sufficient to realize a desired biologic effect. For example, an effective amount of a composition such as is described herein to treat asthma is that amount sufficient to reduce or prevent further induction of Th2 cytokines in order to avoid exacerbation of asthma. Combined with the teachings provided herein, by choosing among the various active compositions and weighing factors such as potency, relative bioavailability, patient body weight, severity of adverse side effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular composition being administered the size of the subject, or the severity of the disease or condition. One of ordinary skill in the art can empirically determine the effective amount of a particular composition and/or other therapeutic agent without necessitating undue experimentation.

The terms "treat," "treated," "treating," and the like, when used herein with respect to a condition characterized by an oxidative stress condition, such as pulmonary fibrosis, refer to administration of the compositions to a subject which may increase the resistance of the subject to development or further development of the condition, to administration of the composition after the subject has developed the condition in order to eliminate or at least control development of the condition, and/or slow the progression of or to reduce the severity of symptoms caused by the condition. When administered to a subject, effective amounts will depend on the particular condition being treated and the desired outcome. A therapeutically effective dose may be determined by those of ordinary skill in the art, for instance, employing factors such as those further described below and using no more than routine experimentation.

For use in therapy, an effective amount of the compositions of the present invention can be administered to a subject by any mode that delivers the composition to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, intravenously, percutaneously, and rectal.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dose of the composition to the subject may be such that a therapeutically effective amount of the composition reaches an active site of the composition within the subject. The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition at the active site. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Subject doses of the compositions described herein for mucosal or local delivery typically range from about 0.1 microgram to 10 mg per administration, which depending on the application could be given daily, weekly, or monthly and any other amount of time therebetween. More typically mucosal or local doses range from about 10 microgram to 5 mg per administration, and most typically from about 100 microgram to 1 mg, with 2 to 4 administrations being spaced days or weeks apart. More typically, doses range from 1 microgram to 10 mg per administration, and most typically 10 microgram to 1 mg, with daily or weekly administrations. Subject doses of the compositions described herein for parenteral delivery for the purpose of treating an oxidative stress condition may be typically 5 to 10,000 times higher than the effective mucosal dose, and more typically 10 to 1,000 times higher, and most typically 20 to 100 times higher. More typically parenteral doses for these purposes range from about 10 microgram to 5 mg per administration, and most typically from about 100 microgram to 1 mg, with 2 to 4 administrations being spaced days or weeks apart. In some embodiments, however, parenteral doses for these purposes may be used in a range of 5 to 10,000 times higher than the typical doses described above. The compositions of the present invention may be administered in multiple doses over extended period of time. For any composition described herein the therapeutically effective amount can be initially determined from animal models. The applied dose can be adjusted based on the relative bioavailability and potency of the administered composition. Adjusting the dose to achieve maximal efficacy based on the methods described above and other methods as are well-known in the art is well within the capabilities of the ordinarily skilled artisan.

The treatments disclosed herein may be given to any subject, for example, a human, or a non-human animal, such as a dog, a cat, a horse, a rabbit, a cow, a pig, a sheep, a goat, a rat (e.g., *Rattus norvegicus*), a mouse (e.g., *Mus musculus*), a guinea pig, a non-human primate (e.g., a monkey, a chimpanzee, a baboon, an ape, a gorilla, etc.), or the like. In one embodiment, the treatment is applied to cells, for example, cells taken from a human subject.

In certain embodiments, a composition of the invention is administered to a subject who has a family history of a condition characterized by an oxidative stress condition, such as pulmonary fibrosis, or to a subject who has a genetic predisposition for the condition. In other embodiments, the composition is administered to a subject who has reached a particular age, or to a subject more likely to get the condition. In yet other embodiments, the compositions is administered to subjects who exhibit symptoms of the condition (e.g., early or advanced). In still other embodiments, the composition may be administered to a subject as a preventive measure. In some embodiments, the composition may be administered to a subject based on demographics or epidemiological studies, or to a subject in a particular field or career.

Administration of a composition of the invention may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the composition within the subject without causing clinically unacceptable adverse effects.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, through parenteral injection or implantation, via surgical administration, or any other method of administration where access to the target by the composition of the invention is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of a composition such as is described herein. Other oral compositions suitable for use with the invention include solutions or suspensions in aqueous or non-aqueous liquids such as a syrup, an elixir, or an emulsion. In another set of embodiments, the composition may be used to fortify a food or a beverage.

In one set of embodiments, the compositions of the invention are administered by inhalation. For administration by inhalation, the compositions for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition and a suitable powder base such as lactose or starch.

Also contemplated herein is pulmonary delivery of certain compositions of the present invention. The compositions may be delivered to the lungs of a mammal while inhaling and traverses across the lung epithelial lining to the blood stream. Other reports of inhaled molecules include Adjei et al., 1990, *Pharmaceutical Research*, 7:565-569; Adjei et al., 1990, *International Journal of Pharmaceutics*, 63:135-144 (leuprolide acetate); Braquet et al., 1989, *Journal of Cardiovascular Pharmacology*, 13(suppl. 5):143-146 (endothelin-1); Hubbard et al., 1989, *Annals of Internal Medicine*, Vol. III, pp. 206-212 (al-antitrypsin); Smith et al., 1989, *J. Clin. Invest.* 84:1145-1146 (a-1-proteinase); Oswein et al., 1990, "Aerosolization of Proteins," *Proceedings of Symposium on Respiratory Drug Delivery II, Keystone*, Colorado, March, (recombinant human growth hormone); Debs et al., 1988, *J. Immunol.*, 140:3482-3488 (interferon-g and tumor necrosis factor alpha) and Platz et al., U.S. Pat. No. 5,284, 656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in some embodiments of the invention are a wide range of mechanical devices designed for pulmonary delivery of therapeutic products, including but not limited to nebulizers, metered dose inhalers, and powder inhalers, all of which are familiar to those skilled in the art.

Some non-limiting specific examples of commercially available devices are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

Certain devices require the use of various formulations suitable for the dispensing of some compositions of the present invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified systems may also be prepared in different formulations depending on the type of chemical modification or the type of device employed.

Formulations suitable for use with a nebulizer, either jet or ultrasonic, will typically comprise a composition as described herein, dissolved in water at a concentration of about 0.1 to 25 mg of biologically active composition per mL of solution. The formulation may also include a buffer and a simple sugar (e.g., for stabilization of the composition and regulation of osmotic pressure). The nebulizer formulation may also contain a surfactant to reduce or prevent surface induced aggregation caused by atomization of the solution in forming the aerosol.

Formulations for use with a metered-dose inhaler device may generally comprise a finely divided powder containing a composition as described herein, suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing a composition as described herein, and may also include a bulking agent, such as lactose, sorbitol, sucrose, or mannitol in amounts which facilitate dispersal of the powder from the device, e.g., 50 to 90% by weight of the formulation. The composition may be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber may be compressed to administer the pharmaceutical composition of the present invention. In a specific embodiment, the chamber is a piston arrangement. Such devices are commercially available.

In another embodiment, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. In some cases, the nasal inhaler will provide a metered amount of the aerosol formulation, for administration of a measured dose of the drug.

For oral administration, the compositions can be formulated readily in some cases by combining the active composition(s) with pharmaceutically acceptable carriers well known in the art. Such carriers allow the compositions of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers, i.e., EDTA for neutralizing internal acid conditions or may be administered without any carriers.

Also specifically contemplated are oral dosage forms of the above compositions. The compositions may be chemically modified, in some embodiments, so that oral delivery of the derivative is efficacious. Generally, the chemical modification contemplated is the attachment of at least one moiety to the composition itself, where said moiety permits (a) inhibition of proteolysis; and/or (b) uptake into the blood stream from the stomach or intestine. Also desired is the increase in overall stability of the component or components and increase in circulation time in the body. Examples of such moieties include:

polyethylene glycol, copolymers of ethylene glycol and propylene glycol, carboxymethyl cellulose, dextran, polyvinyl alcohol, polyvinyl pyrrolidone and polyproline. See, e.g., Abuchowski and Davis, 1981, "Soluble Polymer-Enzyme Adducts," in: *Enzymes as Drugs*, Hocenberg and Roberts, Eds., Wiley-Interscience, New York, N.Y., pp. 367-383; Newmark, et al., 1982, *J. Appl. Biochem.* 4:185-189. Other polymers that could be used are poly-1,3-dioxolane and poly-1,3,6-tioxocane. Preferred for pharmaceutical usage are polyethylene glycol moieties.

For the compositions of the invention (or derivative), the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compositions of the present invention, or by release of the biologically active material beyond the stomach environment, such as in the intestine.

To ensure full gastric resistance a coating impermeable to at least pH 5.0 is usually required. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compositions of the present invention may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into an aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compositions of the present invention, either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compositions may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the compositions described herein in water-soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, the active compositions may be in powder form for constitution with a suitable vehicle, e.g., sterile pyrogen-free water, before use.

The compositions may also be formulated in rectal or vaginal compositions such as suppositories or retention enemas, e.g., containing conventional suppository bases such as cocoa butter or other glycerides.

In addition to the formulations described previously, the compositions may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

In certain embodiments of the invention, the administration of a composition may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time-release, delayed release, sustained release, or controlled release delivery systems. Such systems may avoid repeated administrations of the composition in many cases, increasing convenience to the subject. Many types of release delivery systems are available and known to those of ordinary skill in the art. They include, for example, polymer-based systems such as polylactic and/or polyglycolic acids, polyanhydrides, polycaprolactones and/or combinations of these; nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, and 5,736,152), or diffusional systems in which an active component controls the release rate (for example, as described in U.S. Pat. Nos. 3,854,480, 5,133, 974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Administration of the composition can be alone, or in combination with other therapeutic agents and/or compositions. In certain embodiments of the invention, a composition can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active composition(s) to be administered, but is used as a formulation ingredient, for example, to stabilize or protect the active composition(s) within the composition before use. The carrier may include one or more compatible solid or liquid fillers, diluents or encapsulating substances which are suitable for administration to a human or other vertebrate animal. The term "carrier" denotes an organic or inorganic ingredient, which may be natural or synthetic, with which one or more compositions of the invention are combined to facilitate the application of the composition. The carrier may be co-mingled or otherwise mixed with one or more compositions of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

The formulations of the invention are administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active composition. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In some embodiments, the present invention includes the step of bringing a composition of the invention into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

The compositions of the present invention, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. The term "pharmaceutically acceptable salts" includes salts of the composition, prepared in combination with, for example, acids or bases, depending on the particular compositions found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like. Also, such salts can be prepared as alkaline metal or alkaline earth salts, such as sodium, potassium or calcium salts of the carboxylic acid group.

The present invention also provides any of the above-mentioned compositions in kits, optionally including instructions for use of the composition for the treatment of a condition characterized by an oxidative stress condition, for example, airway inflammation or pulmonary fibrosis. That is, the kit can include a description of use of the composition for participation in any biological or chemical mechanism disclosed herein associated with an oxidative stress condition. The kits can further include a description of activity of the condition in treating the pathology, as opposed to the symptoms of the condition. That is, the kit can include a description of use of the compositions as discussed herein. The kit also can include instructions for use of a combination of two or more compositions of the invention, or instruction for use of a combination of a composition of the invention and one or more other compositions indicated for treatment of the oxidative stress condition. Instructions also may be provided for administering the composition by any suitable technique as previously described, for example, orally, intravenously, pump or implantable delivery device, or via another known route of drug delivery.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

In still another aspect, the invention includes the promotion of one or more of the above-described embodiments, for example, promotion of treatment or prevention of an oxidative stress condition, e.g., by administering, to a subject, a composition comprising an inhibitor of ERp57, an inhibitor of GSTP, and/or a quencher of $H_2O_2$. As used herein, "promoted" includes all methods of doing business, including methods of education, scientific inquiry, academic research, industry activity including pharmaceutical industry activity, and any advertising or other promotional activity including written, oral and electronic communication of any form, associated with the invention.

U.S. patent application Ser. No. 12/664,108, filed Dec. 11, 2009, entitled "Treatments Involving Glutaredoxins and Similar Agents," published as U.S. Patent Application Publication No. 2010/0266566 on Oct. 21, 2010, is incorporated herein by reference:

The following examples are intended to illustrate certain embodiments of the present invention, but do not exemplify the full scope of the invention.

Example 1

These examples demonstrate variations in of Fas behavior, including that distinct pools of Fas exist in cells. As discussed below, upon ligation of surface Fas, a separate pool of latent Fas in the endoplasmic reticulum (ER) underwent rapid oxidative processing characterized by loss of free sulfhydryl content (Fas-SH), and resultant increases in S-glutathionylation of Cys294, leading to increases of surface Fas. Stimulation with FasL rapidly induced associations between Fas, ERp57, and Glutathione S-transferase π (pi) (GSTP), a protein disulfide isomerase, and catalyst of S-glutathionylation, respectively, in the ER. Knockdown or inhibition of ERp57 and/or GSTP1 (one type of GSTP) substantially decreased FasL-induced oxidative processing and S-glutathionylation of Fas, resulting in decreased DISC (death inducing signaling complex) formation, caspase activity, and enhanced survival. Bleomycin-induced pulmonary fibrosis was accompanied by increased interactions between Fas-ERp57-GSTP1, and S-glutathionylation of Fas. Importantly, fibrosis was largely prevented following siRNA-mediated ablation of ERp57 and GSTP1. Collectively, these findings illuminate a regulatory switch, ligand-initiated oxidative processing of latent Fas to control the strength of apoptosis.

ERp57 (PDIA3) belongs to the protein disulfide isomerase (PDI, EC 5.3.4.1) family of oxidoreductases that primarily localizes in the ER and catalyze intra-molecular disulfide bond (—S—S—) formation in proteins to fold into their active/native confirmation. While catalyzing disulfide bonds, the recycling phase of PDI enzymes produces an oxidant, $H_2O_2$, and accumulation of $H_2O_2$ can lead to protein S-glutathionylation. Crystallographic evidence and 3D structure predictions suggest that ectodomain cysteines of TNF receptor family members are in intermolecular disulfide (—S—S—) bonds and may be essential for ligand binding activity. However, no one has studied interaction of Fas or any TNF receptors with PDI family enzymes in order to form disulfide bridges.

Glutathione-S-transferases (GST, EC 2.5.1.18) are classically known as phase II detoxifying enzymes that catalyze the conjugation of GSH to various electrophilic molecules. GSTP may also catalyze protein S-glutathionylation following oxidative and nitrosative stress, and GSTP-catalyzed S-glutathionylation of the sulfenic acid intermediate of 1-Cys-peroxiredoxin may be important in restoration of its function. One example of a GSTP is GSTP1.

ERp57 and GSTP1 may thus be important for post-translational processing of reactive cysteines in proteins. Accordingly, one goal of these examples was to determine whether Fas-SSG occurs during oxidative processing in the ER, and whether this requires the action of ERp57. Another goal was to explore the contribution of GSTP1 as a catalyst of Fas-SSG.

Materials and methods. Cell culture: Murine alveolar type II epithelial cells (C10), or primary lung fibroblasts from wild type (WT), lpr, caspase 3−/− mice and primary mouse tracheal epithelial cells (MTEC) were used. Cells were isolated and propagated using established techniques. Prior to treatment with FasL, C10 cells or fibroblasts were starved in serum free, phenol red free medium for 2 hours. Cells were transfected with plasmids or siRNA using established techniques.

Exposure of cells to FasL: C10 cells were treated with 150 ng/ml FLAG-FasL (Alexis, San Diego, Calif.), plus 0.5 micrograms/ml anti-FLAG cross linking antibody, M2 (Sigma, St. Louis, Mo.). Primary lung fibroblasts and MTECs were treated with 300 ng/ml FasL, plus 1 microgram/ml M2. As reagent controls, cells were treated with M2 alone.

Immunoprecipitation of S-glutathionylated Fas: Immunoprecipitation of S-glutathionylated Fas was performed using established techniques.

Immunoprecipitation of Fas, ERp57 and GSTP1: C10 cells were treated with FasL and M2 for the indicated times. Lysates were prepared in buffer containing 20 mM Tris pH 7.4, 150 mM NaCl, 10% glycerol, and 0.5% NP40 with protease inhibitor cocktail. 500 micrograms of protein were used for immunoprecipitation using anti-Fas (JO2), anti-GSTP1 or ERp57 antibody (1 microgram/ml), using protein G agarose beads. The samples were analyzed by subsequent SDS-PAGE and probing of the western blots. As a reagent control, lysates from cells exposed to FasL+M2 for 1 hour were incubated with isotype control IgG, and subjected to the same procedures.

Cell viability assay: C10 cells or primary lung fibroblasts were plated in 12-well dishes. The MTT (3-(4,5-dimethyl-thiazol-2-yl)-2,5-diphenyltetrazolium bromide) assay was performed using known techniques. Results were obtained from 3 independent experiments conducted in triplicate.

Caspase-Glo assay: Caspase-8 and caspase-3 activities were measured using a Caspase-Glo 8 and Caspase-Glo 3/7 (Promega, Madison, Wis.) reagents, respectively according to the manufacturer's protocol (Promega, Madison, Wis.). Results were expressed in Relative Luminescence Units (RLU), after subtraction of background luminescence values. All results were obtained from 3 independent experiments conducted in triplicate.

DISC isolation and Analysis: DISC isolation was performed using known techniques. Briefly, C10 cells (1×10$^6$ cells/60 mm dish) were transfected. Cells were starved for 2 hours, then treated with FasL (1 microgram/ml) plus cross-linking antibody, M2 (2 micrograms/ml) for 20 minutes at 37° C. Subsequent steps were performed on ice. Cells were washed once with PBS, and lysed for 10 minutes in 500 microliters of lysis buffer.

Cell Fractionation: Cell fractionation was carried out using the Calbiochem ProteoExtractTR (Cat. No. 539790) subcellular proteome extraction kit per the manufacturer's protocol.

Bleomycin model of fibrosis: C57BL/6J mice were instilled with bleomycin (5.0 U/kg) oropharyngeally. Ctr siRNA (scrambled) or siRNA for ERp57 and GSTP1 (10 mg/kg, Thermo Scientific) were administered oropharyngeally 24 hours prior to administration of bleomycin, as well as 5 and 10 days thereafter. Lungs were harvested on day 15 for histology, caspase activity and Sircol collagen assays. Masson's trichrome-stained lung sections were imaged using a Olympus BX50 Light Microscope with QImaging Retiga 2000R digital camera. The images were captured at 10× magnification. All studies were approved by the Institutional Animal Care and Use Committee at the University of Vermont.

Microscopy: Cells were fixed in 4% formalin and permeabilizied with 0.2% Triton-X100 in PBS. Permeabilized cells were blocked in PBS containing 2% BSA for 1 hour. Cells were sequentially incubated with primary antibodies (1:500-rabbit anti-ERp57/mouse anti-Fas) and secondary antibodies (1:1000-anti-rabbit-Alexa Fluor 488/anti-mouse Alexa Fluor 647). The nucleus was stained with DAPI (1:4000). Images were acquired using a Zeiss LSM 510 META Confocal Laser Scanning Imaging System. Images were captured at 40× magnification in oil immersion. The image files were converted to Tiff format. Brightness and contrast were adjusted equally in all images.

Labeling of free sulfhydryls using biotinylated N-ethyl maleimide (MPB): Cells were lysed in HEPES buffer, pH 7.4 containing 0.5% NP40, with 150 micromolar MPB for 1 hour at ambient temperature. Lysates were centrifuged at 14,000 rpm and passed through a microbiospin (Bio-Rad) column to separate free MPB. The eluent whole cell lysate was immunoprecipitated using an anti-Fas antibody and sequentially probed using streptavidin HRP and anti-Fas antibody.

Labeling of cell surface proteins using biotinylated 3,3'-dithiobis-sulfosuccinimidylpropionate (DTSSP): Cells were treated with 0.5 mg of cell impermeable biotinylated DTSSP (Pierce) 30 min prior to harvest in HBSS containing $Ca^{2+}$ and $Mg^{2+}$. Cells were lysed in 20 mM Tris pH 7.4, 150 mM NaCl, 10% glycerol, and 0.5% NP40 with protease inhibitor cocktail. Lysates were centrifuged at 14,000 rpm and passed through a microbiospin (Bio-Rad) column to separate free biotinylated DTSSP. The eluent whole cell lysate was immunoprecipitated using an anti-Fas antibody and sequentially probed using streptavidin HRP and anti-Fas antibody.

Antibodies: Antibodies against the following proteins/molecules were used in this study: rat anti-Fas (Upstate, Lake Placid, N.Y.), rabbit anti-Fas (Santa Cruz), rabbit anti-GSTP1 and rat anti-FADD (MBL, Woburn, Mass.), rat anti-Caspase-8 (Alexis, San Diego, Calif.), rabbit anti-calreticulin and anti-caspase-3 (Cell signaling, Danvers, Mass.), mouse anti-GSH (Virogen, Watertown, Mass.), streptavidin conjugated-HRP (Jackson, West Grove, Pa.), rabbit anti-Prx1, Prx3, Prx4, PrxSO3 (Lab Frontier, Seoul, Korea), goat anti-Grx1 (American Diagnostica, Stamford, Conn.), mouse anti-Flotillin1, JO2 (BD Biosciences, San Jose, Calif.), rabbit/mouse anti-ERp57 and anti-PDI (Enzo Life Sciences, Plymouth Meeting, Pa.; Abcam, Cambridge, Mass.), rabbit anti-ATF6 (Abcam, Cambridge, Mass.) and mouse anti-beta-actin (Sigma, St. Louis, Mo.). The secondary HRP conjugated anti-rabbit and anti-mouse antibodies were from Amersham (Piscataway, N.J.). Anti-rat and anti-goat were from Jackson Laboratories (West Grove, Pa.). All of the fluorophore-conjugated antibodies were from Invitrogen (Carlsbad, Calif.).

Biochemical analysis of extracellular glutathione (GSH): Extracellular GSH was measured using an enzymatic recycling method with a few modifications. Proteins were precipitated from medium by adding 6.5% (w/v) sulfosalicylic acid (SSA). After 10 min, the tubes were centrifuged for 15 min at 2000 g and supernatants were stored at −80° C. Standards (0.5-100 nM GSH equivalent) were prepared by diluting in 10 mM HCl, containing 1.3% of SSA. 5,5'-dithiobis-2-nitrobenzoic acid (DTNB 10 mM), NADPH (2 mM), and GSSG reductase (8.5 IU/ml) were prepared in stock buffer containing 143 mM $NaH_2PO_4$, 6.3 mM EDTA at pH 7.4. The enzymatic reaction was started by addition of 40 microliters/well of GSSG-reductase, and was followed kinetically for 30 sec to 2 min, at a wavelength of 415 nm. The final concentrations of reagents were 0.73 mM DTNB, 0.24 mM NADPH, 0.09% SSA and 1.2 IU/ml GSSG-reductase.

Protein disulfide isomerase (PDI) assay: 10 micrograms of total cell lysates were incubated with folded insulin, fibril protein binding dye for 1 hr. The fluorescence was then measured in a microplate reader set at a excitation of 500 nm and an emission of 603 nm, per the manufacturer's protocol (Proteostat™ PDI assay kit ENZ-51024-KP002). All results were obtained from 3 independent experiments conducted in triplicate.

GST activity assay: The GST activity was determined using a colorimetric activity assay kit (ab65326, Abcam, Cambridge, Mass.) based on the GST-catalyzed reaction between GSH and the GST substrate, CDNB (1-chloro-2,4-dinitrobenzene). The GST-catalyzed formation of CDNB-GSH produced a dinitrophenyl thioether which can be detected spectrophotometrically at 340 nm.

Synthesis of TLK-199 (gamma-glutamyl-S-(benzyl)cysteinyl-R-phenyl glycine diethyl ester): N,N-dimethylformamide and trifluoroacetic acid were purchased from Fisher Scientific (Pittsburgh, Pa.), 2-chlorotrityl chloride resin from Novabiochem (San Diego, Calif.), O-Benzotriazole-N,N,N',N'-tetramethyluronium hexafluorophosphate (HBTU), from RS Synthesis (Louisville, Ky.). Fmoc-D-Phg-OH, Fmoc L-Cys(Bzl)-OH, and Boc-Glu-OBut were purchased from Advanced Chemtech (Louisville, Ky.). TLK199 was synthesized manually via Fmoc protocol on a 40 micromole scale using 2-chlorotrityl chloride resin (1.01 mmol/g loading). Double coupling of Fmoc amino acid derivatives using HBTU activation was employed for peptide elongation.

A typical single coupling procedure was as follows: 20% piperidine/DMF (2×10 min); DMF washes (6×30 s); 5 equiv. Fmoc amino acid and HBTU in 0.4 M NMM/DMF (2×30 min); DMF washes (3×30 s). Cleavage of TLK199 from the resin was accomplished through treatment with 94:2:2:2 TFA/triisopropylsilane (TIPS)/$H_2O$/anisole for 2 hours. Following filtration of the resin, the cleavage supernatant was evaporated to one tenth its original volumes in a stream of nitrogen, followed by precipitation of the crude peptide into cold anhydrous diethyl ether.

Image processing: Digital images were acquired by scanning X-ray film on a photo scanner (perfection 5000; Epson). Photoshop (CS5; Adobe) and Illustrator (CS5; Adobe) were used to assemble the figures. Samples were run on the same gel. In some cases, lanes were assembled for consistency as indicated by vertical black line. When required brightness and contrast were adjusted equally in all lanes.

Statistics: All assays were performed three times in triplicates (9 measurements). Data were analyzed by one-way analysis of variance (ANOVA) using the Bonferroni test to adjust for multiple comparisons or Student's t test where appropriate. Data from multiple experiments were averaged and expressed as mean values+/−SEM.

Example 2

FasL was observed to cause rapid increases in S-glutathionylation of Fas (Fas-SSG), independently of overall changes in redox status or caspase activation. FasL-induced S-glutathionylation of Fas (Fas-SSG) was found to be independent of activation of NADPH oxidases, but was sustained by degradation of Grx1. Protein S-glutathionylation was also dependent on alterations in GSH and glutathione disulfide (GSSG) ratios in the cell. Activation of the Fas pathway can cause GSH efflux from the cell, apparently increasing the levels of cytosolic GSSG.

Following stimulation of cells with FasL in presence of a cross linking antibody, M2, Fas-SSG was observed at 10 to 15 minutes (min) which was sustained until 120 min (FIG. 1A), a time point at which the degradation of Grx1 was detected. The concentration of GSH in culture supernatants increased at 120 min and 240 min post administration of FasL, compared to M2 (0) control samples (FIG. 1B), but not at earlier time points.

In contrast to the requirement of caspase-3 in contributing to increases in Fas-SSG 60 and 120 min following stimulation with FasL, the results in FIG. 1C demonstrate that early increases in Fas-SSG formation observed at 15 or 30 min post stimulation with FasL occurred in cells lacking caspase-3. To determine whether the continuous presence of FasL was required for Fas-SSG, cells were incubated with FasL in the cold for 20 min. FasL was washed away (+wash), or left in the cultures (−wash), and the dishes were returned to 37° C. The results in FIG. 1D demonstrate that binding of FasL to surface Fas was sufficient to induce early but transient Fas-SSG but did not result in cleavage of caspase-3.

Continuous FasL was required to induce sustained Fas-SSG and caspase-3 cleavage. Collectively, these data suggest that early increases in S-glutathionylation of Fas (Fas-SSG) occurred independently of changes in Grx1 content, caspase-3 activity, or efflux of GSH.

Next, whether FasL altered the redox status in specific subcellular compartments was examined by monitoring overoxidation of Prx1, Prx3, or Prx4, which are localized in the cytosol, mitochondria, and endoplasmic reticulum, respectively. Immunoprecipitation (IP) of Prx1, 3, or 4 and subsequent western blots for overoxidized forms of Prxs (PrxSO$_3$) revealed rapid overoxidation of Prx4 which occurred within 10 min following ligation of Fas, and was sustained for at least 120 min. In contrast, overoxidation of Prx3 and 1 also occurred in cells stimulated with FasL, but occurred at later time points compared to Prx4 (FIG. 1E). These findings suggest that FasL induced rapid alterations in the redox status of ER. Despite these findings, FasL did not induce overt ER stress, based upon the absence of detection of the ER stress marker, ATF6, in contrast to cells exposed to the ER stressor, thapsigargin (THP) (FIG. 1F).

Next, experiments were performed to address the oxidative events that preceded Fas-SSG. Formation of a sulfenic acid (—SOH) intermediate is one of the potential oxidative events that can lead to protein S-glutathionylation. Cells were treated with the cell permeable —SOH trapping compound, 5,5-dimethyl-1,3-cyclohexanedione (dimedone), prior to administration of FasL. The results in FIG. 1G demonstrated that formation of Fas-SSG was abolished in cells pre-treated with dimedone, suggesting that Fas-SOH was required for the formation of Fas-SSG.

Accordingly, FIG. 1 shows that early increases in Fas S-glutathionylation (Fas-SSG) occurred independently of efflux of GSH or caspase activation, and were associated with enhanced oxidation in the endoplasmic reticulum (ER). FIG. 1A shows rapid S-glutathionylation of Fas in response to FasL. C10 lung epithelial cells were stimulated with Flag tagged FasL plus anti-Flag (M2) crosslinking antibody, M2 alone (0), and at the indicated times, lysates were prepared and immunoprecipitated (IP) using an anti-GSH antibody. The subsequent western blot was probed with anti-Fas antibody (top panel). The +DTT control reflects lysates prepared from FasL-stimulated cells at 120 min treated with 25 mM DTT prior to IP with the anti-GSH antibody. Bottom panels: Content of Fas and Grx1 in whole cell lysates (WCL). FIG. 1B shows FasL induced GSH efflux. C10 lung epithelial cells were stimulated with FasL plus M2 cross-linking antibody, or M2 alone, and at the indicated times, supernatants were collected. Free GSH was measured. * $p<0.05$ (ANOVA), compared to M2 controls at the same time points.

FIG. 1C shows that early formation of Fas-SSG did not require caspase-3. WT and Caspase3−/− lung fibroblasts were treated with FasL as indicated. Lysates were subjected to IP with anti-GSH antibody, and subsequent western blots were probed with Fas. Bottom panels: content of Fas, total full length caspase-3 (T), cleaved (active, C) caspase-3 and Grx1 in WCL. FIG. 1D shows that the continuous presence of FasL was needed for sustained Fas-SSG and caspase-3 activation. C10 cells were treated with FasL in the cold for 20 min. FasL was washed away (+wash), or left in the dishes (−wash), and cells were then returned to 37° C. for the indicated times. The lysates were processed as in FIG. 1A. FIG. 1E shows an assessment of overoxidation of Prx in response to FasL. Prx1, 3 and 4 were IPed following stimulation with FasL. Western blots were probed for over-oxidized Prx (PrxSO$_3$), and the respective IPed Prx proteins, as a control. FIG. 1F shows that stimulation of cells with FasL did not induce ER stress. C10 lung epithelial cells were stimulated with FasL plus M2, thapsigargin (THP) or M2 antibody/DMSO as controls (Ctr). Cells were lysed after 4 hr. Western blots were probed for the ER stress marker, ATF6, and beta-actin as a loading control. FIG. 1G shows a sulfenic acid intermediate (—SOH) of Fas preceded its S-glutathionylation. Cells were incubated with the sulfenic acid trapping agent, dimedone for 2 hour prior to stimulation of cells with FasL. Lysates were subjected to IP as described with respect to FIG. 1A. Western blots were probed for Fas. Bottom panel: Input Fas in the WCL.

Example 3

FasL induced oxidative processing of Fas, and increased the interaction of ERp57 and GSTP with Fas. The extracellular/ligand binding domains of TNF receptors contained multiple cysteines that form intra-molecular disulfide bridges (—S—S—) to create the ligand binding domain that may be essential for binding of the TNF family of ligands. Murine Fas contains 20 cysteines in its extracellular domain, and 4 cysteines in the cytoplasmic death domain, one of which, Cys294, is the target for S-glutathionylation (FIG. 2A). Based upon the present findings which demonstrated increased oxidation of ER-localized Prx4, whether Fas was oxidatively folded following stimulation with FasL was investigated in this example. Following exposure of cells to FasL, cells were lysed at different time points in the presence of MPB to label protein free sulfhydryls.

Fas was subsequently immunoprecipitated (IP), and its free sulfhydryl content (—SH) assessed by probing western blots with streptavidin conjugated-HRP. In control cells, robust labeling of Fas with MPB was observed, indicating the availability of Fas-SH groups in unstimulated cells. Within 5 min of FasL stimulation, MPB labeling was decreased, and by 10 to 30 min the MPB-labeled Fas could not be immnoprecipitated (FIG. 2B). The loss of Fas-SH groups indicated that pools of latent Fas underwent rapid oxidative processing following stimulation with FasL. However, it is possible that the loss of Fas-SH groups merely precedes S-glutathionylation of Fas at cysteine 294. In order to determine whether loss of Fas-SH groups was linked to S-glutathionylation of cysteine 294, Fas deficient lpr fibroblasts were transfected with wild type Fas or C294A mutant, which cannot be S-glutathionylated. The results in FIG. 2C demonstrated a similar loss of Fas-SH content in cells expressing WT or C294A mutant Fas, indicating that the loss of —SH labeling by MPB was not merely due to S-glutathionylation, but likely due to —S—S— bond formation of multiple cysteines in the extracellular domain.

Intra-molecular disulfide (—S—S—) bond formation of protein cysteines was catalyzed by members of the family of protein disulfide isomerases (PDI). Because of the rapid oxidation of Fas (FIGS. 2B and 2C), whether Fas associates with any of the members of PDI family, by IP, was investigated. The results in FIG. 2D demonstrated a strong association of ERp57 with Fas, upon stimulation with FasL. In contrast, under these conditions, no equivalent increase in interaction between PDI and Fas was observed.

Oxidation of —SH groups to —S—S— by PDIs can generate $H_2O_2$ during their regeneration reaction via the ER-localized oxidoreductase, Ero-1. However, it was demonstrated that Fas-SSG was preceded by Fas-SOH (FIG. 1F), and —SOH could be further S-glutathionylated by GSTP. Thus, whether FasL stimulation increased the interaction of Fas with GSTP1 was examined. Indeed, Fas and GSTP1 co-immunoprecipitated, and their interaction was enhanced following FasL (FIG. 2E). Furthermore, the content of Fas on the cell surface, and SDS resistant, high MW forms of ERp57 and Fas increased immediately after stimulation of cells with FasL (FIGS. 2F and 2G). Collectively, these results demonstrated that rapid oxidation of Fas occurred upon stimulation of cells with FasL, which correlated with associations between the disulfide forming enzyme, ERp57 and Fas, and between the S-glutathionylating enzyme, GSTP1 and Fas.

Epithelial cells can undergo apoptosis via a mitochondrial-dependent amplification pathway, whereas fibroblasts typically undergo apoptosis independently of mitochondria. Indeed, the results in FIG. 2H demonstrated higher increases in mitochondrial-dependent caspase-9 activity in response to FasL in epithelial cells, compared to fibroblasts, while activities of caspases-8 and -3 were comparable in both cell types. The purity of these primary cell cultures was confirmed by western blots for alpha-smooth muscle actin (fibroblasts) and E-cadherin (epithelial cells) (FIG. 2I). Oxidative processing and Fas-SSG were similar in fibroblasts or epithelial cells in response to FasL (FIGS. 2J and 2K), suggesting that Fas oxidations occurred irrespective of an involvement of mitochondria in apoptosis.

Accordingly, FIG. 2 shows FasL induced oxidative processing of latent Fas, and a rapid interaction between ERp57, GSTP1 and Fas. FIG. 2A shows the primary sequence of murine Fas (NP_032013, www.ncbi.nlm.nih.gov/protein/NP_032013.2), showing cysteines (bold) in the ligand binding domain predicted to form disulfide bridges, and the death domain cysteines, including Cys294 which was S-glutathionylated (-SSG). The transmembrane domain is underlined. ELD; extracellular ligand binding domain, CDD; Cytoplasmic Death Domain. FIG. 2B shows FasL induced rapid oxidative processing of latent Fas. C10 lung epithelial cells were treated with FasL. The lysates were labeled with MPB, and IPed using an anti-Fas antibody. Western blots were probed sequentially with streptavidin-conjugated with HRP and anti-Fas antibody (top panels). Bottom: WCL showing content of Fas, ERp57, GSTP1 and beta-actin.

FIG. 2C shows that FasL induced rapid oxidative processing wild type Fas or 38Cys294A mutant Fas. WT and lpr mouse lung fibroblasts were treated with FasL. The lysates were processed as in FIG. 2B. FIG. 2D shows that FasL induced rapid association of latent Fas with ERp57. Cells were treated with FasL as indicated, and lysates subjected to IP using anti-ERp57, anti-PDI antibodies, or pre-immune IgG as a control. Western blots were probed sequentially with anti-Fas and ERp57 (top) or anti-Fas and PDI (bottom) antibodies. FIG. 2E shows that FasL induced rapid association of Fas with GSTP1. Cells were treated with FasL, and lysates were subjected to IP using anti-GSTP1 antibody, or control IgG. Blots were probed sequentially with anti-Fas and GSTP1 antibodies. FIG. 2F shows that FasL increased membrane Fas localization. C10 cells were stimulated with FasL for the indicated times. Prior to the harvest, cells were incubated with biotinylated DTSSP, and lysates subjected to IP with anti-Fas antibody. Blots were probed sequentially with streptavidin-conjugated with HRP and anti-Fas antibody. FIG. 2G shows that FasL induced DTT sensitive high molecular weight forms of ERp57 and Fas. Cells were treated with FasL, and lysates subjected to non-reducing (–DTT) and reducing (+DTT) SDS-PAGE. Blots were probed with ERp57 or Fas antibodies. Approximate molecular weights (MWs) are indicated.

FIG. 2H shows measurement of caspase activities in primary lung fibroblasts and tracheal epithelial cells (MTEC) following stimulation with FasL. FIG. 2I shows confirmation of purity of primary fibroblasts and MTEC, via western blotting for the epithelial marker E-cadherin (E-cad), or the fibroblast marker, alpha-smooth muscle actin (alpha-SMA). Assessment of oxidative processing (FIG. 2J) and S-glutathionylation of Fas (FIG. 2K) in fibroblasts and epithelial cells stimulated with FasL. The lysates were labeled and processed as in FIGS. 2B, and 1A respectively.

Example 4

Interaction of ERp57 and GSTP1 with Fas and S-glutathionylation of Fas in the ER. ERp57 is an ER resident PDI. The presence of Fas and GSTP1 in the ER has not been documented. These examples sought to explore the subcellular compartment in which ERp57, GSTP, and Fas interact, and whether this coincides with Fas-SSG. For this purpose, cells were fractionated into cytosol/plasma membrane (pm), ER, and nuclear fractions, as identified by the markers Prx1/Flotillin1, Calreticulin (CRT) and Histone H3 respectively. As expected, in control cells (0), ERp57 was found only in fraction 2, which also contained the ER marker protein, CRT (FIG. 3A). Fas was readily detectable in the ER (fraction 2), as well as nucleus (fraction 3) and to some extent in cytosol/pm (fraction 1). GSTP1 was found in both cytosol/pm and ER fractions, although predominantly in the cytosol/pm. Within 15 min of stimulation of cells with FasL, the Fas content in the cytosol/pm increased (FIG. 3A). The S-glutathionylated form of Fas was first detected in the ER by 10 min, and started to appear in cytosol/pm at 15 min and was sustained at least 30 min after FasL stimulation (FIG. 3A, top lanes).

Next, the subcellular interaction of Fas with ERp57, using confocal laser scanning microscopy was evaluated. The results in FIG. 3B demonstrate that in control cells, no co-localization of Fas and ERp57 was detected. However, increased co-localization of Fas and ERp57 was apparent within 10 min post stimulation with FasL, with further increases apparent by 30 min post stimulation. IP of GSTP1 from fractions 1 and 2 indicated some association between Fas and GSTP in the ER in control cells, and increased associations upon stimulation with FasL which were predominantly in the ER by 10 min. However, 15 and 30 min post FasL, interactions of Fas and GSTP1 increased in both ER and cytosolic/pm fractions (FIG. 3C).

Next, these examples sought to characterize whether the movement of Fas-SSG from ER to cytosol/pm was dependent on anterograde transport, using an anterograde transport blocking agent, Brefeldin A. In Brefeldin A-treated cells stimulated with FasL, Fas-SSG remained restricted to the ER fraction, and no Fas was detected in the cytosol/pm, in contrast to cells treated with DMSO vehicle control (FIG. 3D). In aggregate, these results demonstrated that in response to ligation of surface Fas, oxidative processing, and S-glutathionylation of a separate pool of Fas occurs in the ER, in association with increased interactions between Fas, ERp57 and GSTP1.

FIG. 3 shows localization of ERp57, Fas and GSTP1, and S-glutathionylation of Fas in the ER. FIG. 3A shows that C10 cells were stimulated with FasL, and cells were fractionated into cytosolic/plasma membrane (1), endoplasmic reticulum (ER, 2), and nucleus (3). Proteins from each fraction were subjected to IP using anti-GSH antibody. Western blots were probed for Fas. 25 micrograms of total protein from each fractions were separated on a SDS-PAGE and probed for Fas, ERp57, GSTP1, Prx1 (cytosolic protein), Flotillin1 (Flot1, plasma membrane protein), calreticulin (CRT, an ER restricted protein), histone H3 (nuclear marker). FIG. 3B shows that Fas co-localizes with the ER protein, ERp57. Cells were treated with FasL, stained with ERp57, Fas, and the nuclear marker, DAPI. Merged images indicate co-localization of Fas and ERp57. FIG. 3C shows that stimulation with FasL causes an enhanced interaction between GSTP1 and Fas. Proteins from fractions characterized in FIG. 3A were subjected to IP using anti-GSTP1 antibodies, or control IgG. FIG. 3D shows that Fas was S-glutathionylated in ER and then translocated to cytosol/PM fraction. Epithelial cells were treated with FasL, in the presence or absence of Brefeldin A. Cells were fractionated as in FIG. 3A, and proteins from each fraction were subjected to IP using anti-GSH antibody. Western blots were probed for Fas. 25 micrograms of total protein from each fraction was separated on a SDS-PAGE and probed for Fas, ERp57, GSTP1, Prx1 (cytosol), Flot1 (plasma membrane), CRT (ER), H3 (nucleus).

Example 5

Knockdown of ERp57 and GSTP1 decreased oxidative processing, and S-glutathionylation of Fas, and increased cell survival. In order to address the functional importance of ERp57 and GSTP in oxidative processing, S-glutathionylation of Fas and ramifications for apoptosis, ERp57 and GSTP1 were ablated individually or simultaneously in epithelial cells. The results in FIG. 4A demonstrated an almost complete loss of Fas-SSG in cells lacking ERp57 upon ligation of Fas, compared to siRNA controls (top panel). Smaller, but consistent decreases in FasL-stimulated Fas-SSG were also observed following siRNA-mediated knockdown of GSTP1. Simultaneous ablation of both ERp57 and GSTP1 resulted in a complete loss of detectable Fas-SSG in response to FasL (FIG. 4A bottom panel), demonstrating that the coordinate action of ERp57 and GSTP1 was required for FasL-induced Fas-SSG. Previous experiments demonstrated a rapid FasL-induced loss of sulfhydryl content of Fas (Fas-SH, FIG. 2B).

Since a complete loss of Fas-SSG was observed following siRNA-mediated ablation of ERp57 and GSTP1 siRNA samples, Fas-SH in cells lacking ERp57 and GSTP1 following stimulation with FasL was assessed. Consistent with results in FIG. 2B, a rapid loss of Fas-SH occurred in response to FasL in control siRNA-transfected cells (FIG. 4B). In contrast, following knockdown of both ERp57 and GSTP1, Fas-SH content was equivalent to unstimulated cells up to 15 min post stimulation with FasL, although some decreases in sulfhydryl content were apparent at later time points (FIG. 4B).

Next, whether the decreases in oxidative-processing and S-glutathionylation of Fas in cells lacking ERp57 and GSTP had any impact on death inducing signaling complex (DISC) formation was tested. Cells were exposed to the FasL oligomerizing antibody (M2) alone, or FasL plus M2. As expected, IP of the DISC demonstrated associations between Fas, FADD and caspase-8, following incubation of cells with FasL, but not M2 alone. Interestingly, both ERp57 and GSTP also co-immunoprecipitated with the DISC in FasL-treated cells. In cells with decreased levels of ERp57 and GSTP1, functional DISC assembly did not occur following Fas ligation, based upon the absence of Fas, FADD and pro-caspase-8 that co-immunoprecipitated with FasL, compared to control siRNA (FIG. 4C). siRNA based ablation of ERp57 or GSTP1 resulted in decreased activities of caspases 8 and 3 and diminished cell death in response to FasL, compared to control siRNA (FIGS. 4D to 4F). Simultaneous knockdown of ERp57 and GSTP1 resulted in further decreases in caspase 8 and 3 activities upon Fas ligation, and further rescued cells from FasL-induced death, compared to knockdown of proteins individually (FIGS. 4D to 4F).

Thus, FIG. 4 shows that knockdown of ERp57 and GSTP1 decreased FasL induced S-glutathionylation of Fas and increased cell survival. FIG. 4A shows that cells were transfected with Control (Ctr), ERp57 (top panel), GSTP1, or ERp57 and GSTP1 (bottom panel) siRNAs. Cells were exposed to FasL, and cell lysates processed as in FIG. 1A. Western blots from WCL were sequentially probed for Fas, ERp57 and GSTP1. FIG. 4B shows FasL-induced oxidative processing of Fas was attenuated in cells lacking ERp57 and GSTP1. Cells were treated with FasL, and lysates processed as in FIG. 2B. FIG. 4C shows that FasL-induced formation of DISC was attenuated in cells lacking ERp57 and GSTP1. Cells were transfected with ERp57 and GSTP1 siRNA (E+P), and 24 hours later were exposed to FasL+M2 cross-linking antibody (FL), or M2 alone for 30 min. Cell lysates were subjected to IP of the DISC. Western blots were sequentially probed for Fas, FADD, procaspase 8, ERp57 and GSTP1. WCL: assessment of the same proteins in whole cell lysates, as a control. FIGS. 4D to 4F shows knockdown of ERp57 and GSTP1 decreased caspase 8 (FIG. 4D), and caspase-3 activity (FIG. 4E), and increased cell survival (FIG. 4F) by MTT assay, 4 hours following stimulation with FasL. * $p<0.05$ ANOVA compared to Ctr siRNA groups. # $p<0.05$ compared to ERp57 or GSTP1 siRNA groups.

Example 6

Pharmacologic inhibition of ERp57 and GSTP1 decreased Fas-SSG and caspase activation: next, the contribution of the catalytic activities of ERp57 and GSTP in mediating S-glutathionylation of Fas, and subsequent activation of caspases, was assessed. Epithelial cells were incubated with thiomuscimol, a known inhibitor of PDIs, or its inactive analog muscimol for 2 hrs at 37° C. Thiomuscimol-treated cells showed a ~50% decrease in insulin reducing activity as compared to the muscimol controls (FIG. 5A).

Figure 5B:
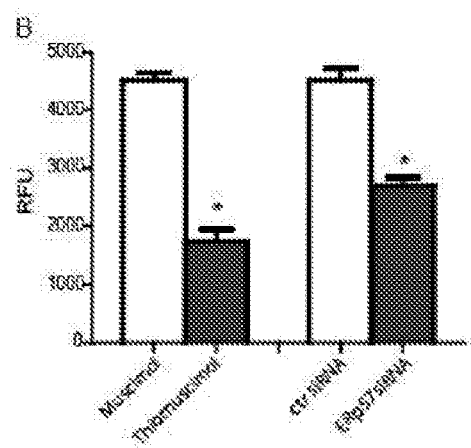
Figure 5C:
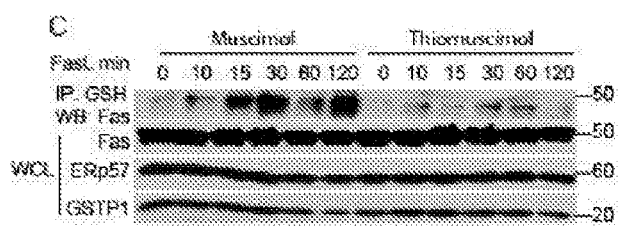

Validation of the insulin reducing assay using ERp57 siRNA demonstrated a ~45% decrease in insulin reducing activity as compared to control siRNA-transfected cells, indicating that a substantial amount thiomuscimol-inhibitable insulin reducing activity may be due to ERp57 (FIG. 5B). Thiomuscimol significantly attenuated Fas-SSG in response to FasL, compared to muscimol controls (FIG. 5C), with corresponding decreases in activities of caspases 8 and 3 (FIGS. 5D and 5E).

TLK199 (gamma-glutamyl-S-(benzyl)cysteinyl-R-phenyl glycine diethyl ester) is a highly specific inhibitor of GSTP. The results in FIG. 5F demonstrate that incubation of cells with 50 micromolar of TLK199 resulted in an 80% decrease in GSTP activity. FasL-mediated increases in Fas-SSG, caspase 8 and 3 activities were all diminished in cells exposed to TLK199 (FIGS. 5G to 5I). Collectively, these results demonstrated that the coordinate catalytic activities of ERp57 and GSTP contribute to Fas-SSG and subsequent activation of caspases.

In addition to Fas, the extracellular/ligand binding domains of other members of the TNF receptor superfamily also contained cysteines that form intra-molecular disulfide bridges (—S—S—) to create the ligand binding domain. These experiments therefore determined whether ERp57-mediated oxidative processing regulates TNFR-dependent apoptosis. Cells were incubated with the ERp57 inhibitor, thiomuscimol prior to stimulation with TNF-alpha in the presence of cycloheximide (CHX) to induce apoptosis. The results in FIG. 5J demonstrate that TNF-alpha/CHX-mediated activation of caspase-3 was significantly decreased by thiomuscimol, while the muscimol control did not affect apoptosis. These findings suggested that ER-dependent oxidative processing also affected apoptosis induced via other members of the TNFR superfamily.

Thus, FIG. 5 shows that inhibition of ERp57 and GSTP1 decreased FasL-induced S-glutathionylation of Fas and caspase activity. FIG. 5A shows that cells were incubated with the PDI inhibitor, thiomuscimol (10 micromolar) or its inactive analog muscimol (10 micromolar) for 1 hour, prior to determination of PDI activity, using an insulin reduction assay. The results are expressed as relative fluorescence units (RFU). * $p<0.05$ (Student t-test) compared to muscimol treated cells. FIG. 5B shows determination of PDI activity (as in FIG. 6A) in thiomuscimol and ERp57 siRNA-treated cells. * $p<0.05$ (Student t-test) compared to control cells. FIG. 5C shows that cells were pre-incubated with the PDI inhibitor thiomuscimol (10 micromolar), or its inactive analog muscimol (10 micromolar) for 1 hour prior to stimulation with FasL for the indicated times. Cell lysates were processed as in FIG. 1A to determine Fas-SSG (FIGS. 5D and 5E). Inhibition of ERp57 decreased caspase 8, and caspase 3 activities. * $p<0.05$ ANOVA, compared to muscimol-treated cells.

Figure 5F:
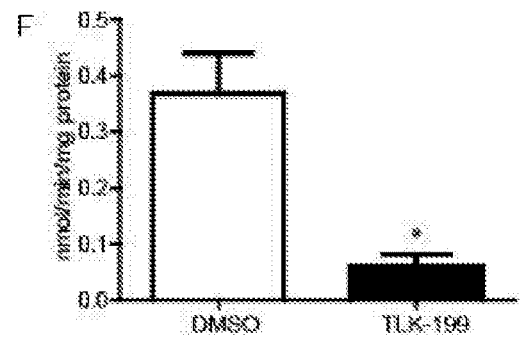
Figure 5G:
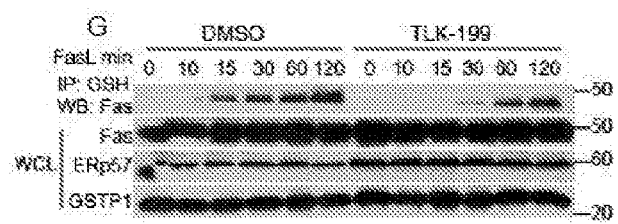
Figure 5H:
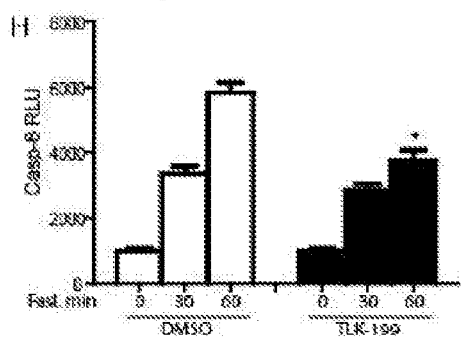

FIG. 5F shows that cells were incubated with GSTP inhibitor, TLK-199 (50 micromolar) or 0.2% DMSO for 2 hours, prior to determination of the GSTP activity, using the CDNB-GST assay. The results are expressed as nmol of CDNB oxidized/min/mg protein. * $p<0.05$ (Student t-test) compared to DMSO controls. FIG. 5G shows that TLK199 decreased Fas-SSG. Cells were pre-incubated TLK-199 or DMSO for 2 hours, prior to stimulation with FasL. Lysates were processed as in FIG. 1A. Inhibition of GSTP decreased the activities of caspases 8 (FIG. 5H) and 3 (FIG. 5I) induced by FasL. * $p<0.05$ ANOVA, compared to DMSO controls. FIG. 5J shows the effect of thiomuscimol on TNF-alpha plus cycloheximide (CHX) induced caspase-3 activation. Mus: muscimol control. * $p<0.05$ ANOVA, compared to TNF-alpha+CHX controls.

Example 7

Overexpression of Prx4 decreased S-glutathionylation of Fas, caspase activation and cell death. Based on the findings demonstrating that FasL led to increased oxidation of ER-localized Prx4 and subsequent Fas-SSG, it was speculated that overexpression of Prx4 would quench the $H_2O_2$ produced in response to oxidative folding, and decrease Fas-SSG. As expected, overexpression of Prx4 resulted in higher levels of Prx4 overoxidation, reflective of quenching of $H_2O_2$ (FIG. 6A). Overexpression of Prx4 did not inhibit FasL-mediated oxidative folding of Fas (FIG. 6B), but almost completely prevented subsequent Fas-SSG (FIG. 6C). Furthermore, overexpression of Prx4 also resulted in significantly decreased caspase 8 and 3 activities, and increased cell survival in response to FasL (FIGS. 6D to 6F). These findings suggested that Prx4 acts downstream of oxidative folding of Fas, and that $H_2O_2$ produced during oxidative folding may be required for subsequent formation of Fas-SSG.

FIG. 6 shows that Prx4 did not affect Fas-SH, but decreased FasL-induced Fas-SSG and apoptosis. FIG. 6A shows an assessment of overoxidation of Prx4 (top) following its overexpression (bottom). FIG. 6B shows the lack of impact of Prx4 overexpression on oxidative processing of Fas. Cells were transfected with pCDNA3 and Prx4 plasmids, subsequently treated with FasL. The lysates were processed as in FIG. 2B. Bottom panel: Prx4 and ERp57 content in WCL. Prx4 overexpression decreased Fas-SSG (FIG. 6C), caspase 8 and 3 activities (FIGS. 6D and 6E) and cell death (FIG. 6F) in response to FasL. * $p<0.05$ ANOVA compared to M2 controls, # $p<0.05$ compared to pCDNA3.

Example 8

Figure 7A:
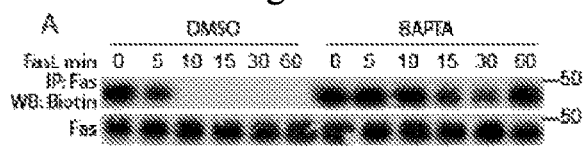
FIGS. 7A-7E illustrate chelation of $Ca^{2+}$, in yet another embodiment of the invention.
Figure 7D:
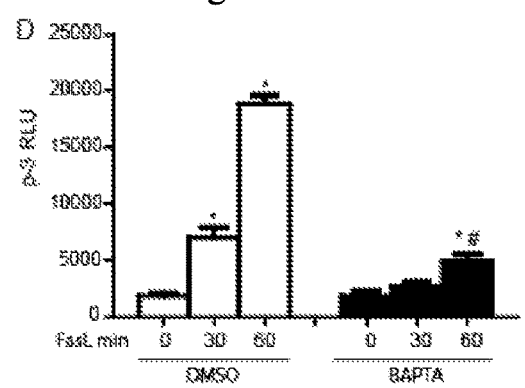
Figure 7B:
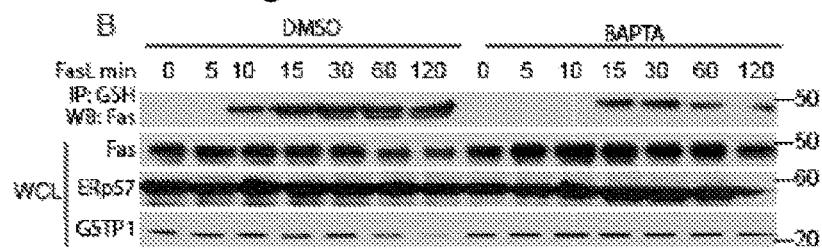
Figure 7C:
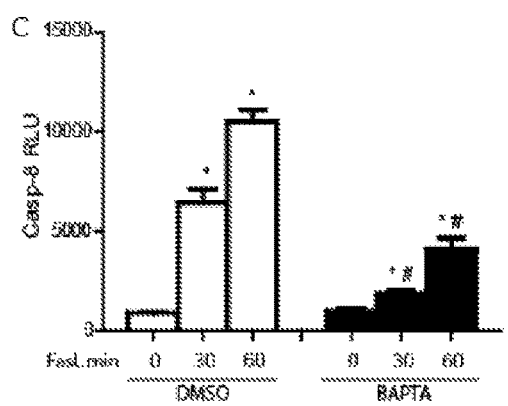
Figure 7E:
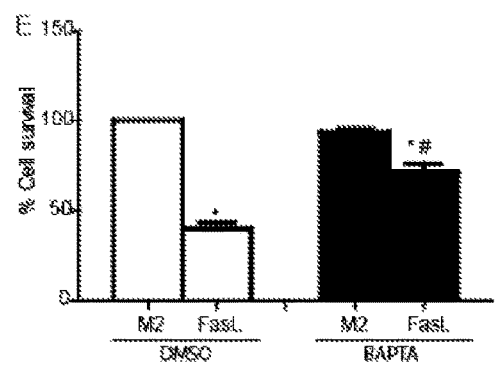

Calcium chelation abolished oxidative folding, and decreased Fas-SSG, caspase activation and apoptosis. Calcium ($Ca^{2+}$) may play a critical role in Fas-mediated apoptosis. To determine whether oxidative processing of Fas was dependent on calcium, cells were incubated with a cell permeable $Ca^{2+}$ chelator, BAPTA-AM (Tocris). The results in FIGS. 7A and B demonstrated that pre-incubation of cells with BAPTA-AM completely prevented the loss of Fas-SH groups observed in response to FasL, and substantially diminished Fas-SSG. Furthermore, chelation of $Ca^{2+}$ resulted in decreased caspase 8 and 3 activities, and increased cell survival in response to FasL (FIGS. 7C to 7E). These findings suggested that a $Ca^{2+}$-dependent signal was required for the induction of oxidative processing and S-glutathionylation of latent Fas in the ER.

FIG. 7 shows that the chelation of $Ca^{2+}$ decreased FasL-induced oxidative processing of Fas, Fas-SSG, and epithelial cell apoptosis. BAPTA inhibited oxidative processing of Fas (FIG. 7A), and decreased Fas-SSG (FIG. 7B), caspase 8 and 3 activities (FIGS. 7C and 7D), and cell death (FIG. 7E) in response to FasL. * $p<0.05$ ANOVA compared to M2 controls, # $p<0.05$ compared to DMSO treated cells.

Example 9

Overexpression of ERp57 and GSTP enhanced S-glutathionylation of Fas, caspase activity and cell death. In order to determine the impact of overexpression of ERp57 or GSTP1 in FasL-induced cell death, cells were transfected with pcDNA3, GSTP1, or ERp57 cDNAs. The fractionation of cells overexpressing both ERp57 and GSTP1 demonstrated that by 10 min of FasL stimulation, Fas-SSG and total Fas content were already increased in the cytosol/pm fraction (fraction 1) in contrast to pcDNA3 transfected cells were Fas-SSG remained restricted to the ER (fraction 2), and Fas was largely absent from the cytosol/pm (FIG. 8A). Overexpression of ERp57 or GSTP1 individually resulted in small increases in FasL-induced activation of caspases 8 and 3, as well as cell death, compared to pcDNA3-transfected cells. However, overexpression of both ERp57 and GSTP1 simultaneously lead to further increases in FasL-induced activities of caspases 8 and 3, and resulted in enhanced cell death, compared to individual control groups (FIGS. 8B to 8D). In aggregate, these findings demonstrate that ERp57 and GSTP1 enhanced the kinetics of Fas-SSG and movement of Fas into the membrane/cytosol, and cooperated to enhance caspase activation and cell death.

FIG. 8 shows that the overexpression of ERp57 and GSTP1 increased the kinetics of translocation of S-glutathionylated Fas from the ER to the cytosolic/plasma membrane fraction, and decreased cell survival in response to FasL. FIG. 8A shows an assessment of Fas-SSG in cytosol/ plasma membrane fractions (fraction 1), ER (fraction 2), and nucleus (fraction 3), in cells overexpressing ERp57 and GSTP. C10 lung epithelial cells were transfected with pCDNA3, or pERp57 plus pGSTP1 plasmids for 24 hours, prior to exposure to FasL. Cell fractionations were prepared, for IP using anti-GSH antibody and WB as described in FIG. 3A. Overexpression of ERp57 and GSTP1 increased caspase-8 (FIG. 8B) and caspase-3 (FIG. 8C) activities and cell death (FIG. 8D). * p<0.05 compared to pcDNA3 control groups. # p<0.05 compared to cells transfected with ERp57 or GSTP1 individually (ANOVA).

Example 10

Knockdown of ERp57 and GSTP1 inhibited bleomycin-induced pulmonary fibrosis in mice. It was sought to corroborate the functional relevance of these observations in the bleomycin model of acute lung injury and fibrosis, which require functional Fas. C57BL/6 mice were instilled oropharengeally with siRNA for ERp57 and GSTP1 (E+G siRNAs), one day prior to administration of bleomycin (BLM), and 5 and 10 days thereafter. The results in FIGS. 9A and 9B demonstrated that increases in collagen content in lung tissue, and histopathology 15 days post administration of bleomycin were significantly attenuated in mice receiving ERp57 and GSTP1 siRNAs, compared to scrambled siRNA instilled mice. Similarly, increases in caspase-8 and -3 activities following instillation of bleomycin were also significantly inhibited in mice following knock-down of ERp57 and GSTP1 compared to Ctr siRNA instilled mice (FIGS. 9C and 9D).

Next, it was sought to determine whether bleomycin-induced Fas-SSG was decreased in mice lacking ERp57 and GSTP1. The results in FIG. 9E demonstrated robust increases in Fas-SSG in mice instilled with Ctr siRNA after 15 days following administration of BLM, while very little Fas-SSG was detected in mice following knock-down of ERp57 and GSTP1. Immunoprecipitation of Fas from lung tissues of BLM-treated animals showed strong interactions with ERp57 and GSTP1, which were not detected in the PBS control group. As expected, the overall content of ERp57 and GSTP in lung tissue, and their interaction with Fas was decreased in response to their siRNA-mediated ablation (FIGS. 9E and 9F). Altogether, these results illuminate the potential patho-physiological relevance of ERp57 and GSTP mediated S-glutathionylation of Fas in fibrotic disease, in which a causal role of Fas has been implicated.

FIG. 9 shows that the knockdown of ERp57 and GSTP1 ameliorated bleomycin-induced pulmonary fibrosis in mice. C57Bl/6 mice were instilled with control (Ctr) siRNA or ERp57+GSTP1 siRNA (E+G) 1 day prior and 5 and 10 days post bleomycin (BLM) or PBS instillations. FIG. 9A shows a histological assessment of collagen using Masson's trichrome. FIG. 9B shows a quantitative assessment of collagen content in the upper right lung lobe of mice instilled with siRNAs and bleomycin or PBS, by the Sircol assay. The results are expressed as micrograms collagen/lobe, and are representative of 6-7 mice/group. * p<0.05, compared to PBS groups, # p<0.05, compared to BLM-Ctr siRNA instilled mice (ANOVA). Measurement of caspase 8 (FIG. 9C), and 3 (FIG. 9D) activities in lung homogenates 15 days following instillation of PBS or BLM. * p<0.05, compared to PBS groups, # p<0.05 compared to the Ctr siRNA group (ANOVA).

FIG. 9E shows Fas-SSG in lung tissue, 15 days following instillation with bleomycin (BLM). FIG. 9F shows associations between Fas, ERp57, and GSTP 15 days following instillation with BLM. Lung lysates were subjected to IP using anti-Fas antibody or IgG as a control. WB were probed for Fas, ERp57 and GSTP1. FIG. 9G shows a model depicting initial FasL-Fas signaling to ER, by a $Ca^{2+}$-dependent mechanism. FasL-triggered oxidative processing of a latent pool of Fas in the ER mediates its S-glutathionylation (Fas-SSG), via the coordinate actions of ERp57 and GSTP. This in turn increased surface Fas, promoted DISC assembly, caspase activation and amplified cell death.

Example 11

The regulation of biological processes by redox active enzymes is becoming increasingly appreciated, and regulatory roles for dynamic cysteine oxidations such as disulfide (—S—S—) and mixed disulfide (S-SG) bonds are emerging. However, the relevance of these events, precise molecular targets, and the redox active enzymes involved in apoptotic signaling are still obscure. These investigations into the involvement of a redox-based mechanism in Fas-dependent apoptosis demonstrated that initial ligation of Fas triggers subsequent S-glutathionylation of Fas (Fas-SSG) at Cys294, which was sustained by caspase-dependent degradation of the de-glutathionylating enzyme, Grx1. Fas-SSG enhances DISC assembly, promotes further activation of caspases, and represents a regulatory mechanism to amplify apoptosis.

However, the biochemical events that are responsible for the S-glutathionylation of Fas remained unknown. The results from the present studies demonstrated that Fas-SSG occurred rapidly, prior to overall changes in the cellular redox state, measured by efflux of GSH, overoxidation of Prx1 and Prx3. It was also demonstrated that early increases in Fas-SSG were independent of caspase-3, and occurred prior to degradation of Grx1. Instead, S-glutathionylation of Fas was catalyzed by coordinated actions of two enzymes, i.e. ERp57 and GSTP1 (FIG. 9G). The present studies illuminated that distinct pools of Fas exist, including a latent pool, which is not oxidatively processed into the mature form capable of ligand binding. Following stimulation with FasL, latent Fas is processed by ERp57 in the ER. During oxidative processing of Fas in the ER, $H_2O_2$ is produced which in turn facilitates S-glutathionylation of Cys294 via a GSTP-dependent mechanism. These findings illuminate a new dimension to the knowledge of Fas-induced apoptosis, and suggest a regulatory switch-ligand-initiated oxidative processing of latent Fas to control the strength of the apoptotic signal. These results also demonstrated that highly compartmentalized changes in the cellular redox environment mediate S-glutathionylation of Fas.

The signaling events that initiate oxidative processing of Fas in the ER upon stimulation of cells with FasL remain unclear. Given the rapid loss of free thiol content of Fas, already apparent after 5 min, these events are induced rapidly, and are unlikely to require internalization of Fas, nor assembly of the DISC (FIG. 4C). Previous work showed that FasL-induced increases in phospholipase C-γ1 (C-gamma-1) (PLC-γ1) activity mediate rapid release of $Ca^{2+}$ via $IP_3R$ channels, which were required for Fas-mediated apoptosis. These results confirmed not only the role of $Ca^{2+}$ in Fas-mediated apoptosis, but also demonstrated a putative role for $Ca^{2+}$ in mediating rapid ERp57-dependent oxidative processing in the ER.

The extracellular ligand binding domain of Fas has 20 cysteines, which may be present as 10 intra-molecular disulfide bridges (—S—S—). These experiments showed that ERp57 plays an important role in the oxidative folding of Fas, ultimately leading to S-glutathionylation of Cys294. The loss of free sulfhydryl content of Fas, in cells expressing Cys294Ala mutant Fas which cannot be S-glutathionylated (FIG. 2C), and the preferential impact of overexpression of Prx4 on attenuating Fas-SSG but not the loss of Fas-SH following FasL (FIGS. 6B and 6C) suggested that oxidative processing of Fas by ERp57 and S-glutathionylation may be separate events. Without wishing to be bound by any theory, increases in $H_2O_2$ formed during regeneration of oxidized ERp57 may potentially cause a sulfenic acid intermediate of Cys294. In turn, GSTP may catalyze S-glutathionylation of the sulfenic acid intermediate of Cys294 (FIG. 9G).

ERp57 acts as a cofactor in assembly of heavy chain of major histocompatibility complex class I molecules, regulation of calcium homeostasis, quality control of newly synthesized glycoproteins and folding of influenza virus hemagglutinin. ERp57 also plays a role in hyperoxia-induced apoptosis of mouse lung endothelial cells. Along with PDI, ERp57 mediates misfolded protein-induced apoptosis in neuronal cells via accumulation at the ER-associated mitochondrial membrane, and facilitation of oligomerization of Bak via intra-molecular cysteine oxidation to form —S—S— bridges, leading to permeabilization of the outer membrane of mitochondria.

Ero-1 has been identified as a key enzyme in the disulfide formation pathway and plays a role in regenerating oxidized PDI. Ero-1 transfers electrons from thiol substrates, such as PDI, to molecular oxygen, producing $H_2O_2$, and oxidizing PDI. Without wishing to be bound by any theory, Ero-1-derived $H_2O_2$ may be responsible for the formation of a sulfenic acid intermediate (—SOH) of Fas, which in turn is the target of GSTP-catalyzed S-glutathionylation. Similar to Ero-1, Prx4 has also been suggested to be an alternative acceptor of electrons from PDI family enzymes. However, the results from these studies demonstrated that Prx4 was overoxidized rapidly in response to FasL, and that overexpression of Prx4 decreased Fas-SSG and apoptosis. These results suggested that excess $H_2O_2$ produced by rapid oxidative processing of Fas could be the cause of this oxidation instead of Prx4 being an electron acceptor in FasL-induced oxidative processing.

GSTs may act as regulators of molecular pathways that control cell division and apoptosis. Interestingly, GSTP1 may glutathionylate a 1-Cys peroxiredoxin Prx6 during its regeneration cycle via a —SOH intermediate. Furthermore, Gstp−/− mouse embryonic fibroblasts may show significantly less glutathionylation of proteins during oxidative and nitrosative stress. The results of the present study demonstrated that FasL induced a rapid interaction of Fas with GSTP1, which initially was observed in the ER compartment where Fas-SSG occurs, and subsequently in the cytosolic/plasma membrane fraction (FIG. 3C). siRNA mediated knockdown or pharmacological inhibition of GSTP1 both resulted in decreased Fas-SSG, although not in a complete lack of S-glutathionylation. The residual increases in Fas-SSG that were observed may be the result of incomplete knock-down or inhibition of GSTP. Alternatively it is possible that spontaneous reaction between GSH and the Fas-SOH accounts for the observed increased in S-glutathionylation of Fas in the absence of GSTP1 at the later time points. Furthermore, the enhanced ratio of glutathione disulfide relative to reduced glutathione present in the ER, may also contribute to Fas-SSG in the absence of GSTP.

Lung fibrosis is believed to be a manifestation of dysregulated repair following injury, in association with impaired re-epithelialization, and aberrant myofibroblast activation and proliferation. Numerous pathways have been linked to the pathogenesis of fibrotic lung disease, including Fas, which contributes to apoptosis of lung epithelial cells. A redox imbalance also has been implicated in disease pathogenesis. The results from the present study demonstrated that during the pathogenesis of bleomycin-induced lung fibrosis, interactions between Fas, ERp57 and GSTP occurred, together with marked increases in Fas-SSG, and increased activities of caspases 8 and 3. Furthermore, it was demonstrated in the present study that ERp57 and GSTP were causally linked to lung fibrogenesis induced by bleomycin, suggesting that ER-linked ERp57 and GSTP-catalyzed S-glutathionylation of Fas may be an important mechanism that drives disease pathogenesis. ER stress is often observed in subjects with familial idiopathic pulmonary fibrosis, who have mutations in surfactant protein C. Increased oxidative processing and S-glutathionylation of Fas may be induced in those subjects, which would enable new therapeutic strategies to alleviate the progression of fibrosis.

Example 12

This example demonstrates the role of ERp57 in a mouse model of house dust mite induced asthma, and the potential utility of thiomuscimol therein.

Figure 10A:
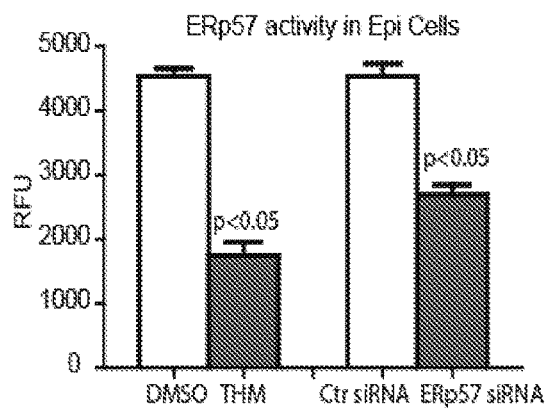
FIGS. 10A-10B illustrate the inhibition of ERp57 in cells, in another embodiment of the invention.
Figure 10B:
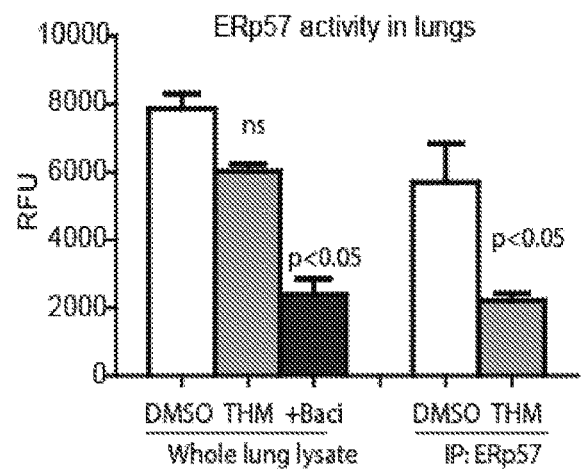

In FIG. 10, ERp57 inhibition by thiomuscimol (THM) is demonstrated. Briefly, epithelial cells were either treated with DMSO and THM or Ctr siRNA and ERp57 siRNA. These figures show mice that were treated with DMSO and THM. As a positive control for the assay, the lysates were incubated with Bacitracin for 2 hrs. As can be seen in these figures, cells exposed to thiomuscimol or bacitracin exhibited inhibition of ERp57, as measured by RFU.

Figure 11A:
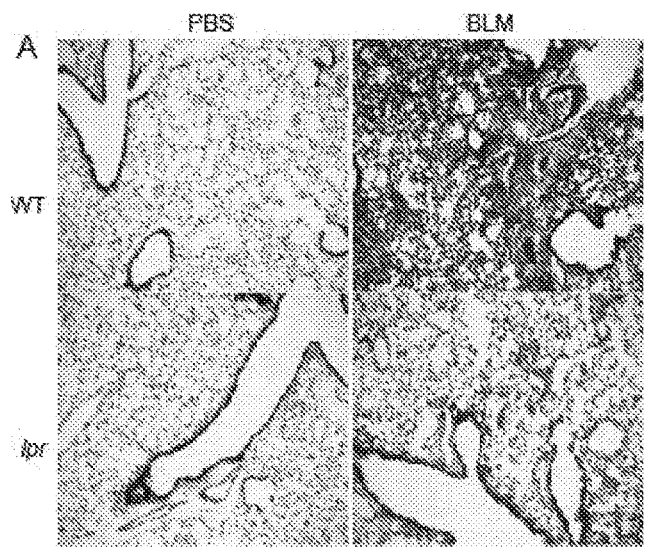
FIGS. 11A-11D illustrate bleomycin-induced collagen deposition and caspase activity, in yet another set of embodiments.
Figure 11B:
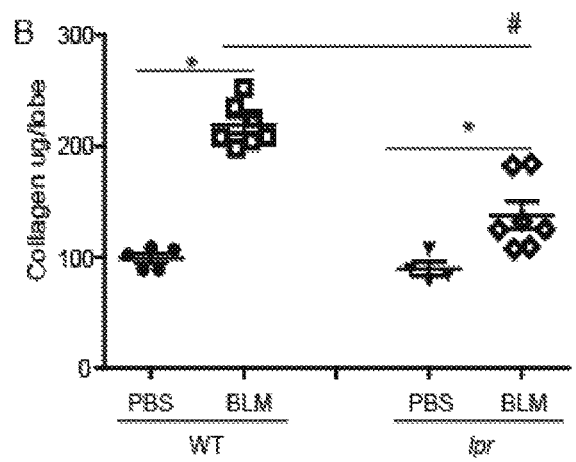
Figure 11C:
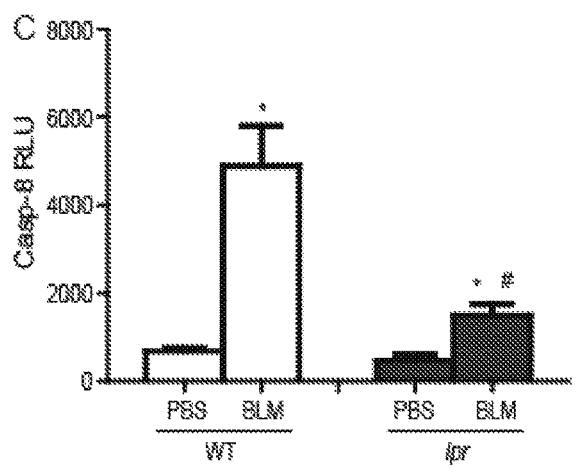
Figure 11D:
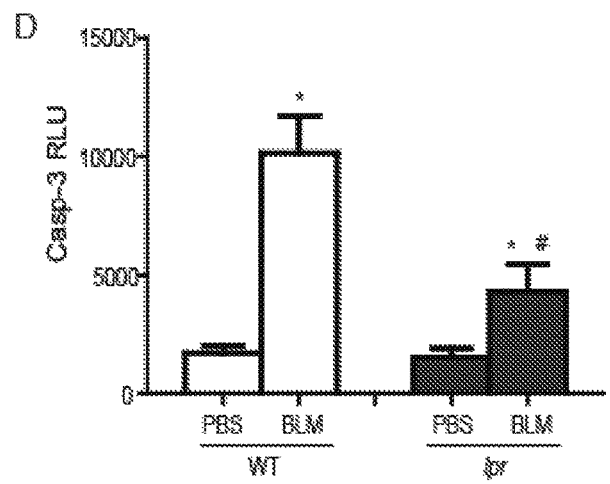

FIGS. 11A and 11B demonstrate bleomycin (BLM) induces collagen deposition in WT mice as compared to lpr mice. FIGS. 11C and 11D demonstrate bleomycin (BLM) induced caspase activity is increased in WT mice as compared to lpr mice.

In FIG. 12A, Fas S-glutathionylation was increased in bleomycin (BLM) treated WT mice but not in lpr, while FIG. 12B shows that Fas-GSTP1-ERp57 interacts in bleomcyin (BLM) treated WT mice but not in lpr.

Thus ERp57 and GSTP were causally linked to collagen deposition and caspase activity that was induced by bleomycin, again suggesting that ER-linked ERp57 and GSTP-catalyzed S-glutathionylation of Fas may be an important mechanism that drives certain types of diseases, such as the requirement of Fas in lung fibrosis, the role of ERp57 in a mouse model of house dust mite induced asthma, and the potential utility of thiomuscimol therein, and Fas-S-glutathionylation in patients with idiopathic pulmonary fibrosis.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   administering, to a subject at risk of genetically-linked familial pulmonary fibrosis, an inhibitor of GSTP, wherein the inhibitor comprises gamma-glutamyl-S-(benzyl)cysteinyl-R-phenyl glycine diethyl ester, wherein the subject has an identified risk factor of developing pulmonary fibrosis, and wherein the risk of pulmonary fibrosis is genetically linked.

2. The method of claim 1, wherein the risk of pulmonary fibrosis is created by a genetic mutation in a surfactant protein carried in the subject.

3. The method of claim 1, wherein the inhibitor further comprises a siRNA.

4. The method of claim 1, wherein the inhibitor comprises an inhibitor of GSTP1.

5. The method of claim 1, further comprising administering, to the subject, an inhibitor of ERp57.

6. The method of claim 1, further comprising administering, to the subject, a quencher of $H_2O_2$.

7. The method of claim 5, wherein the inhibitor of ERp57 is 16F16.

8. The method of claim 1, wherein the subject carries a mutation in surfactant protein C.

* * * * *

UNITED STATES PATENT AND TRADEMARK OFFICE
CERTIFICATE OF CORRECTION

PATENT NO. : 10,688,150 B2
APPLICATION NO. : 15/874136
DATED : June 23, 2020
INVENTOR(S) : Yvonne M. Janssen-Heininger et al.

Page 1 of 1

It is certified that error appears in the above-identified patent and that said Letters Patent is hereby corrected as shown below:

On the Title Page

Item (73) should read:
(73) Assignee: The University of Vermont and State Agricultural College, Burlington, VT (US)

Signed and Sealed this
First Day of September, 2020

Andrei Iancu
*Director of the United States Patent and Trademark Office*

SEQUENCE LISTING

<160> NUMBER OF SEQ ID NOS: 18

<210> SEQ ID NO 1
<211> LENGTH: 327
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (295)..(295)
<223> OTHER INFORMATION: Xaa is Cys attached to an S-glutathionylated
      moiety, i.e., -S-S-G

<400> SEQUENCE: 1

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Leu Cys Ser Pro Gly Glu Lys
    50                  55                  60

Lys Val Glu Asp Cys Lys Thr Asn Gly Gly Lys Pro Ile Cys Thr Ser
65                  70                  75                  80

Cys Thr Glu Gly Lys Glu Tyr Met Asp Lys His Tyr Ala Asp Lys
                85                  90                  95

Cys Arg Arg Cys Thr Leu Cys Asp Glu Glu His Gly Leu Glu Val Glu
                100                 105                 110

Thr Asn Cys Thr Pro Thr Gln Asn Thr Lys Cys Lys Cys Lys Pro Asp
            115                 120                 125

Phe Tyr Cys Asp Ser Ser Gly Cys Glu His Cys Val Arg Cys Thr Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Arg Lys Tyr Arg Lys Arg
            180                 185                 190

Lys Cys Trp Lys Arg Arg Gln Asp Asp Pro Glu Ser Arg Thr Ser Ser
    195                 200                 205

His Glu Thr Ile Pro Met Asn Ala Ser Asn Leu Ser Leu Ser Lys Tyr
210                 215                 220

Ile Pro Arg Ile Ala Glu Asp Met Thr Ile Gln Glu Ala Lys Lys Phe
225                 230                 235                 240

Ala Arg Glu Asn Asn Ile Lys Glu Gly Lys Ile Asp Glu Ile Ile His
                245                 250                 255

Asp Asn Ile Gln Asp Thr Ala Glu Gln Lys Val Gln Leu Leu Leu Cys
            260                 265                 270

Trp Tyr Gln Ser His Gly Lys Ser Asp Ala Tyr Gln Asp Leu Ile Lys
        275                 280                 285

Gly Leu Lys Lys Ala Glu Xaa Arg Arg Thr Leu Asp Lys Phe Gln Asp
    290                 295                 300

Met Val Gln Lys Asp Leu Gly Asn Ser Thr Pro Asp Ile Gly Asn Glu
305                 310                 315                 320

Asn Glu Gly Gln Cys Leu Glu
                325

<210> SEQ ID NO 2
<211> LENGTH: 19
<212> TYPE: RNA
<213> ORGANISM: Artificial Sequence
```

```
<220> FEATURE:
<223> OTHER INFORMATION: Synthetic Polynucleotide

<400> SEQUENCE: 2
cuuacuauga uguggacua                                                        19

<210> SEQ ID NO 3
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 3
ccucaugacg gaagaua                                                          17

<210> SEQ ID NO 4
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 4
cauaugaagu caaggguuu                                                        19

<210> SEQ ID NO 5
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 5
guaugaaggu ggccgugaa                                                        19

<210> SEQ ID NO 6
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 6
aggcaaagcu uucaucgug                                                        19

<210> SEQ ID NO 7
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 7
gguaagaaug acuacguga                                                        19

<210> SEQ ID NO 8
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 8
cauacaccau ugucuacuu                                                        19
```

```
<210> SEQ ID NO 9
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 9
cauacaccau ugucuacuu                                              19

<210> SEQ ID NO 10
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 10
auagauaccu ggaugcaag                                              19

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 11

Cys Pro Tyr Cys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 12

Cys Ser Tyr Cys
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 13

Cys Gly Phe Ser
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 14

Cys Pro Phe Cys
1

<210> SEQ ID NO 15
<211> LENGTH: 5
```

-continued

```
<212> TYPE: PRT
<213> ORGANISM: Artificial Sequence
<220> FEATURE:
<223> OTHER INFORMATION: Synthetic Peptide

<400> SEQUENCE: 15

Gly Cys Ser Cys Gly
1               5

<210> SEQ ID NO 16
<211> LENGTH: 505
<212> TYPE: PRT
<213> ORGANISM: Homo sapiens

<400> SEQUENCE: 16

Met Arg Leu Arg Arg Leu Ala Leu Phe Pro Gly Val Ala Leu Leu Leu
1               5                   10                  15

Ala Ala Ala Arg Leu Ala Ala Ser Asp Val Leu Glu Leu Thr Asp
                20                  25                  30

Asp Asn Phe Glu Ser Arg Ile Ser Asp Thr Gly Ser Ala Gly Leu Met
                35                  40                  45

Leu Val Glu Phe Phe Ala Pro Trp Cys Gly His Cys Lys Arg Leu Ala
    50                  55                  60

Pro Glu Tyr Glu Ala Ala Ala Thr Arg Leu Lys Gly Ile Val Pro Leu
65                  70                  75                  80

Ala Lys Val Asp Cys Thr Ala Asn Thr Asn Thr Cys Asn Lys Tyr Gly
                    85                  90                  95

Val Ser Gly Tyr Pro Thr Leu Lys Ile Phe Arg Asp Gly Glu Glu Ala
                100                 105                 110

Gly Ala Tyr Asp Gly Pro Arg Thr Ala Asp Gly Ile Val Ser His Leu
            115                 120                 125

Lys Lys Gln Ala Gly Pro Ala Ser Val Pro Leu Arg Thr Glu Glu Glu
130                 135                 140

Phe Lys Lys Phe Ile Ser Asp Lys Asp Ala Ser Ile Val Gly Phe Phe
145                 150                 155                 160

Asp Asp Ser Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Glu Tyr Asp Asp Asn Gly Glu Gly Ile Ile Leu Phe Arg Pro
        195                 200                 205

Ser His Leu Thr Asn Lys Phe Glu Asp Lys Thr Val Ala Tyr Thr Glu
    210                 215                 220

Gln Lys Met Thr Ser Gly Lys Ile Lys Lys Phe Ile Gln Glu Asn Ile
225                 230                 235                 240

Phe Gly Ile Cys Pro His Met Thr Glu Asp Asn Lys Asp Leu Ile Gln
                245                 250                 255

Gly Lys Asp Leu Leu Ile Ala Tyr Tyr Asp Val Asp Tyr Glu Lys Asn
            260                 265                 270

Ala Lys Gly Ser Asn Tyr Trp Arg Asn Arg Val Met Met Val Ala Lys
        275                 280                 285

Lys Phe Leu Asp Ala Gly His Lys Leu Asn Phe Ala Val Ala Ser Arg
    290                 295                 300

Lys Thr Phe Ser His Glu Leu Ser Asp Phe Gly Leu Glu Ser Thr Ala
305                 310                 315                 320

Gly Glu Ile Pro Val Val Ala Ile Arg Thr Ala Lys Gly Glu Lys Phe
```

```
                        325                 330                 335
Val Met Gln Glu Glu Phe Ser Arg Asp Gly Lys Ala Leu Glu Arg Phe
                340                 345                 350

Leu Gln Asp Tyr Phe Asp Gly Asn Leu Lys Arg Tyr Leu Lys Ser Glu
            355                 360                 365

Pro Ile Pro Glu Ser Asn Asp Gly Pro Val Lys Val Val Ala Glu
        370                 375                 380

Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
                405                 410                 415

Lys Glu Leu Gly Glu Lys Leu Ser Lys Asp Pro Asn Ile Val Ile Ala
                420                 425                 430

Lys Met Asp Ala Thr Ala Asn Asp Val Pro Ser Pro Tyr Glu Val Arg
                435                 440                 445

Gly Phe Pro Thr Ile Tyr Phe Ser Pro Ala Asn Lys Lys Leu Asn Pro
            450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Lys Pro Lys
                    485                 490                 495

Lys Lys Lys Lys Ala Gln Glu Asp Leu
                500                 505

<210> SEQ ID NO 17
<211> LENGTH: 210
<212> TYPE: PRT
<213> ORGANISM: Homo sapiens

<400> SEQUENCE: 17

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
                20                  25                  30

Val Val Thr Val Glu Thr Trp Gln Glu Gly Ser Leu Lys Ala Ser Cys
            35                  40                  45

Leu Tyr Gly Gln Leu Pro Lys Phe Gln Asp Gly Asp Leu Thr Leu Tyr
        50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190
```

Phe Leu Ala Ser Pro Glu Tyr Val Asn Leu Pro Ile Asn Gly Asn Gly
            195                 200                 205

Lys Gln
    210

<210> SEQ ID NO 18
<211> LENGTH: 271
<212> TYPE: PRT
<213> ORGANISM: Homo sapiens

<400> SEQUENCE: 18

Met Glu Ala Leu Pro Leu Leu Ala Ala Thr Thr Pro Asp His Gly Arg
1               5                   10                  15

His Arg Arg Leu Leu Leu Leu Pro Leu Leu Phe Leu Leu Pro Ala
            20                  25                  30

Gly Ala Val Gln Gly Trp Glu Thr Glu Glu Arg Pro Arg Thr Arg Glu
            35                  40                  45

Glu Glu Cys His Phe Tyr Ala Gly Gly Gln Val Tyr Pro Gly Glu Ala
    50                  55                  60

Ser Arg Val Ser Val Ala Asp His Ser Leu His Leu Ser Lys Ala Lys
65                  70                  75                  80

Ile Ser Lys Pro Ala Pro Tyr Trp Glu Gly Thr Ala Val Ile Asp Gly
                85                  90                  95

Glu Phe Lys Glu Leu Lys Leu Thr Asp Tyr Arg Gly Lys Tyr Leu Val
            100                 105                 110

Phe Phe Phe Tyr Pro Leu Asp Phe Thr Phe Val Cys Pro Thr Glu Ile
        115                 120                 125

Ile Ala Phe Gly Asp Arg Leu Glu Glu Phe Arg Ser Ile Asn Thr Glu
    130                 135                 140

Val Val Ala Cys Ser Val Asp Ser Gln Phe Thr His Leu Ala Trp Ile
145                 150                 155                 160

Asn Thr Pro Arg Arg Gln Gly Gly Leu Gly Pro Ile Arg Ile Pro Leu
                165                 170                 175

Leu Ser Asp Leu Thr His Gln Ile Ser Lys Asp Tyr Gly Val Tyr Leu
            180                 185                 190

Glu Asp Ser Gly His Thr Leu Arg Gly Leu Phe Ile Ile Asp Asp Lys
        195                 200                 205

Gly Ile Leu Arg Gln Ile Thr Leu Asn Asp Leu Pro Val Gly Arg Ser
    210                 215                 220

Val Asp Glu Thr Leu Arg Leu Val Gln Ala Phe Gln Tyr Thr Asp Lys
225                 230                 235                 240

His Gly Glu Val Cys Pro Ala Gly Trp Lys Pro Gly Ser Glu Thr Ile
                245                 250                 255

Ile Pro Asp Pro Ala Gly Lys Leu Lys Tyr Phe Asp Lys Leu Asn
            260                 265                 270